United States Patent
Altarac et al.

(10) Patent No.: US 12,035,946 B2
(45) Date of Patent: Jul. 16, 2024

(54) INTERSPINOUS SPACER

(71) Applicant: VertiFlex, Inc., Carlsbad, CA (US)

(72) Inventors: Moti Altarac, Irvine, CA (US); Shawn Tebbe, Leixlip (IE); Joey Camia Reglos, Lake Forest, CA (US); Yang Cheng, Foothill Ranch, CA (US); Murali P. Kadaba, San Carlos, CA (US); Daniel H. Kim, Houston, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/082,502

(22) Filed: Dec. 15, 2022

(65) Prior Publication Data

US 2023/0124277 A1 Apr. 20, 2023

Related U.S. Application Data

(63) Continuation-in-part of application No. 17/522,350, filed on Nov. 9, 2021, which is a continuation of
(Continued)

(51) Int. Cl.
*A61F 2/44* (2006.01)
*A61B 17/00* (2006.01)
(Continued)

(52) U.S. Cl.
CPC ...... *A61B 17/7062* (2013.01); *A61B 17/7065* (2013.01); *A61B 2017/00004* (2013.01); *A61B 2017/00557* (2013.01); *A61F 2/0077* (2013.01)

(58) Field of Classification Search
CPC ............ A61B 17/7062; A61B 17/7065; A61B 17/7064; A61B 17/7067; A61B 17/7068; A61B 17/7074; A61F 2/44
See application file for complete search history.

(56) References Cited

U.S. PATENT DOCUMENTS

| 2,248,054 A | 7/1941 | Becker |
| 2,677,369 A | 5/1954 | Knowles |

(Continued)

FOREIGN PATENT DOCUMENTS

| CA | 268461 A | 2/1927 |
| CN | 2794456 Y | 7/2006 |

(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.

(Continued)

*Primary Examiner* — Christopher D. Prone
(74) *Attorney, Agent, or Firm* — Branch Partners PLLC; Bruce E. Black

(57) ABSTRACT

An implantable spacer for placement between adjacent spinous processes in a spinal motion segment is provided. The spacer includes a body defining a longitudinal axis and passageway. A first arm and a second arm are connected to the body. Each arm has a pair of extensions and a saddle defining a U-shaped configuration for seating a spinous process therein. Each arm has a proximal caming surface and is capable of rotation with respect to the body. An actuator assembly is disposed inside the passageway and connected to the body. When advanced, a threaded shaft of the actuator assembly contacts the caming surfaces of arms to rotate them from an undeployed configuration to a deployed configuration. In the deployed configuration, the distracted adjacent spinous processes are seated in the U-shaped portion of the arms.

19 Claims, 24 Drawing Sheets

Related U.S. Application Data application No. 15/966,287, filed on Apr. 30, 2018, now Pat. No. 11,229,461, which is a continuation of application No. 14/887,201, filed on Oct. 19, 2015, now Pat. No. 9,956,011, which is a continuation of application No. 13/619,195, filed on Sep. 14, 2012, now Pat. No. 9,161,783, which is a continuation of application No. 12/220,427, filed on Jul. 24, 2008, now Pat. No. 8,277,488, which is a continuation-in-part of application No. 12/217,662, filed on Jul. 8, 2008, now Pat. No. 8,273,108, which is a continuation-in-part of application No. 12/148,104, filed on Apr. 16, 2008, now Pat. No. 8,292,922, said application No. 12/220,427 is a continuation-in-part of application No. 11/593,995, filed on Nov. 7, 2006, now Pat. No. 8,425,559, which is a continuation-in-part of application No. 11/582,874, filed on Oct. 18, 2006, now Pat. No. 8,128,662.

(51) Int. Cl.
*A61B 17/70* (2006.01)
*A61F 2/00* (2006.01)

(56) References Cited

U.S. PATENT DOCUMENTS

| | | |
|---|---|---|
| 2,933,114 A | 4/1960 | Bystrom |
| 3,242,120 A | 3/1966 | Steuber |
| 3,486,505 A | 12/1969 | Morrison |
| 3,648,691 A | 3/1972 | Lumb et al. |
| 3,780,733 A | 12/1973 | Martinez |
| 3,986,383 A | 10/1976 | Petteys |
| 4,545,374 A | 10/1985 | Jacobson |
| 4,632,101 A | 12/1986 | Freeland |
| 4,685,447 A | 8/1987 | Iversen et al. |
| 4,799,484 A | 1/1989 | Smith et al. |
| 4,863,476 A | 9/1989 | Sheppard |
| 4,877,020 A | 10/1989 | Vich |
| 4,895,564 A | 1/1990 | Farrell |
| 4,986,831 A | 1/1991 | King |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere et al. |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A | 7/1997 | Samani et al. |
| 5,654,599 A | 8/1997 | Casper |
| 5,658,335 A | 8/1997 | Allen |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin et al. |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,763 B1 | 7/2001 | Castro |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 | 8/2002 | Elberg et al. |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |

(56) References Cited

U.S. PATENT DOCUMENTS

| | | | |
|---|---|---|---|
| 6,572,617 B1 | 6/2003 | Senegas et al. |
| 6,575,981 B1 | 6/2003 | Boyd et al. |
| 6,579,281 B2 | 6/2003 | Palmer |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps |
| 6,610,065 B1 | 8/2003 | Branch et al. |
| 6,610,091 B1 | 8/2003 | Reiley |
| 6,616,673 B1 | 9/2003 | Stone et al. |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | Dicarlo |
| 6,712,819 B2 | 3/2004 | Zucherman et al. |
| 6,716,215 B1 | 4/2004 | David et al. |
| 6,716,245 B2 | 4/2004 | Pasquel et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Amin et al. |
| 6,974,478 B2 | 12/2005 | Reiley et al. |
| 6,976,988 B2 | 12/2005 | Ralph et al. |
| 7,011,685 B2 | 3/2006 | Amin |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquel et al. |
| 7,097,648 B1 | 8/2006 | Globerman |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,187,064 B2 | 6/2007 | Matge et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell et al. |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Amin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu |
| 7,727,233 B2 | 6/2010 | Blackwell et al. |
| 7,727,241 B2 | 6/2010 | Gorensek et al. |
| 7,731,751 B2 | 6/2010 | Butler |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Amin |
| 7,763,028 B2 | 7/2010 | Lim |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Amin et al. |
| 7,811,322 B2 | 10/2010 | Amin et al. |
| 7,811,323 B2 | 10/2010 | Amin et al. |
| 7,811,324 B2 | 10/2010 | Amin et al. |
| 7,811,330 B2 | 10/2010 | Amin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Amin et al. |
| 7,837,687 B2 | 11/2010 | Harp |
| 7,837,688 B2 | 11/2010 | Boyer et al. |
| 7,837,700 B2 | 11/2010 | Harp |
| 7,837,711 B2 | 11/2010 | Bruneau et al. |
| 7,837,734 B2 | 11/2010 | Zucherman et al. |

(56) References Cited

U.S. PATENT DOCUMENTS

| | | |
|---|---|---|
| 7,846,183 B2 | 12/2010 | Blain |
| 7,846,185 B2 | 12/2010 | Carls et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Salsberg |
| 7,942,830 B2 | 5/2011 | Salsberg |
| 7,955,392 B2 | 6/2011 | Dewey et al. |
| 7,985,246 B2 | 7/2011 | Trieu et al. |
| 8,012,207 B2 | 9/2011 | Kim |
| 8,025,684 B2 | 9/2011 | Garcia-Bengochea et al. |
| 8,057,513 B2 | 11/2011 | Kohm et al. |
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Salsberg |
| 8,613,747 B2 | 12/2013 | Altarac et al. |
| 8,628,574 B2 | 1/2014 | Altarac et al. |
| 8,696,671 B2 | 4/2014 | Salsberg |
| 8,734,477 B2 | 5/2014 | Salsberg |
| 8,740,948 B2 | 6/2014 | Reglas |
| 8,845,726 B2 | 9/2014 | Tebbe et al. |
| 8,864,828 B2 | 10/2014 | Altarac et al. |
| 8,882,772 B2 | 11/2014 | Salsberg |
| 8,894,653 B2 | 11/2014 | Salsberg |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglas |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 9,532,812 B2 | 1/2017 | Altarac et al. |
| 9,572,603 B2 | 2/2017 | Altarac et al. |
| 9,675,303 B2 | 6/2017 | Choi |
| 9,861,398 B2 | 1/2018 | Altarac et al. |
| 9,956,011 B2 | 5/2018 | Altarac et al. |
| 10,058,358 B2 | 8/2018 | Altarac et al. |
| 10,080,587 B2 | 9/2018 | Altarac et al. |
| 2001/0031965 A1 | 10/2001 | Zucherman et al. |
| 2002/0022856 A1 | 2/2002 | Johnson |
| 2002/0042607 A1 | 4/2002 | Palmer |
| 2002/0116009 A1 | 8/2002 | Fraser |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum |
| 2003/0074075 A1 | 4/2003 | Thomas et al. |
| 2003/0083747 A1 | 5/2003 | Winterbottom et al. |
| 2003/0105466 A1 | 6/2003 | Ralph et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0148028 A1 | 7/2004 | Ferree |
| 2004/0167625 A1 | 8/2004 | Beyar et al. |
| 2004/0220568 A1 | 11/2004 | Zucherman et al. |
| 2004/0225295 A1 | 11/2004 | Zubok et al. |
| 2004/0249378 A1 | 12/2004 | Saint Martin et al. |
| 2005/0021042 A1 | 1/2005 | Marnay |
| 2005/0049708 A1 | 3/2005 | Atkinson et al. |
| 2005/0075634 A1 | 4/2005 | Zucherman et al. |
| 2005/0090822 A1 | 4/2005 | DiPoto et al. |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0209698 A1 | 9/2005 | Gordon |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0030860 A1 | 2/2006 | Peterman |
| 2006/0036258 A1 | 2/2006 | Zucherman et al. |
| 2006/0064107 A1 | 3/2006 | Bertagnoli et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0122458 A1 | 6/2006 | Bleich |
| 2006/0122620 A1 | 6/2006 | Kim |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247658 A1 | 11/2006 | Pond, Jr. et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |

(56) References Cited

U.S. PATENT DOCUMENTS

| | | | |
|---|---|---|---|
| 2007/0032790 A1* | 2/2007 | Aschmann | A61B 17/7065 606/90 |
| 2007/0055237 A1 | 3/2007 | Edidin et al. | |
| 2007/0055246 A1 | 3/2007 | Zucherman et al. | |
| 2007/0073289 A1 | 3/2007 | Kwak et al. | |
| 2007/0100340 A1 | 5/2007 | Lange et al. | |
| 2007/0100366 A1 | 5/2007 | Dziedzic et al. | |
| 2007/0123863 A1 | 5/2007 | Winslow et al. | |
| 2007/0123904 A1 | 5/2007 | Stad et al. | |
| 2007/0161991 A1 | 7/2007 | Altarac et al. | |
| 2007/0161993 A1 | 7/2007 | Lowery et al. | |
| 2007/0173818 A1 | 7/2007 | Hestad et al. | |
| 2007/0173821 A1 | 7/2007 | Trieu | |
| 2007/0173822 A1 | 7/2007 | Bruneau et al. | |
| 2007/0173823 A1 | 7/2007 | Dewey et al. | |
| 2007/0173832 A1 | 7/2007 | Tebbe et al. | |
| 2007/0173939 A1 | 7/2007 | Kim et al. | |
| 2007/0179500 A1 | 8/2007 | Chin et al. | |
| 2007/0185490 A1 | 8/2007 | Implicito | |
| 2007/0191857 A1 | 8/2007 | Allard et al. | |
| 2007/0191948 A1 | 8/2007 | Amin et al. | |
| 2007/0191991 A1 | 8/2007 | Addink | |
| 2007/0198045 A1 | 8/2007 | Morton et al. | |
| 2007/0198091 A1 | 8/2007 | Boyer et al. | |
| 2007/0203493 A1 | 8/2007 | Zucherman et al. | |
| 2007/0203495 A1 | 8/2007 | Zucherman et al. | |
| 2007/0203496 A1 | 8/2007 | Zucherman et al. | |
| 2007/0203497 A1 | 8/2007 | Zucherman et al. | |
| 2007/0203501 A1 | 8/2007 | Zucherman et al. | |
| 2007/0208345 A1 | 9/2007 | Marnay et al. | |
| 2007/0208346 A1 | 9/2007 | Marnay et al. | |
| 2007/0208366 A1 | 9/2007 | Pellegrino et al. | |
| 2007/0210018 A1 | 9/2007 | Wallwiener | |
| 2007/0225706 A1 | 9/2007 | Clark et al. | |
| 2007/0225724 A1 | 9/2007 | Edmond | |
| 2007/0225807 A1 | 9/2007 | Phan et al. | |
| 2007/0225814 A1 | 9/2007 | Atkinson et al. | |
| 2007/0233068 A1 | 10/2007 | Bruneau et al. | |
| 2007/0233074 A1 | 10/2007 | Anderson et al. | |
| 2007/0233076 A1 | 10/2007 | Trieu | |
| 2007/0233077 A1 | 10/2007 | Khalili | |
| 2007/0233081 A1 | 10/2007 | Pasquel et al. | |
| 2007/0233082 A1 | 10/2007 | Chin et al. | |
| 2007/0233083 A1 | 10/2007 | Abdou | |
| 2007/0233084 A1 | 10/2007 | Betz et al. | |
| 2007/0233088 A1 | 10/2007 | Edmond | |
| 2007/0233089 A1 | 10/2007 | DiPoto et al. | |
| 2007/0233096 A1 | 10/2007 | Garcia-Bengochea | |
| 2007/0233098 A1 | 10/2007 | Mastrorio et al. | |
| 2007/0233129 A1 | 10/2007 | Bertagnoli et al. | |
| 2007/0250060 A1 | 10/2007 | Anderson et al. | |
| 2007/0260245 A1 | 11/2007 | Malandain et al. | |
| 2007/0265623 A1 | 11/2007 | Malandain et al. | |
| 2007/0265624 A1 | 11/2007 | Zucherman et al. | |
| 2007/0265625 A1 | 11/2007 | Zucherman et al. | |
| 2007/0265626 A1 | 11/2007 | Seme | |
| 2007/0270822 A1 | 11/2007 | Heinz | |
| 2007/0270823 A1 | 11/2007 | Trieu et al. | |
| 2007/0270824 A1 | 11/2007 | Lim et al. | |
| 2007/0270826 A1 | 11/2007 | Trieu et al. | |
| 2007/0270827 A1 | 11/2007 | Lim et al. | |
| 2007/0270828 A1 | 11/2007 | Bruneau et al. | |
| 2007/0270829 A1 | 11/2007 | Carls et al. | |
| 2007/0270834 A1 | 11/2007 | Bruneau et al. | |
| 2007/0272259 A1 | 11/2007 | Allard et al. | |
| 2007/0276368 A1 | 11/2007 | Trieu et al. | |
| 2007/0276369 A1 | 11/2007 | Allard et al. | |
| 2007/0276372 A1 | 11/2007 | Malandain et al. | |
| 2007/0276373 A1 | 11/2007 | Malandain | |
| 2007/0276390 A1 | 11/2007 | Salsberg | |
| 2007/0276493 A1 | 11/2007 | Malandain et al. | |
| 2007/0276496 A1 | 11/2007 | Lange et al. | |
| 2007/0276497 A1 | 11/2007 | Anderson | |
| 2007/0276500 A1 | 11/2007 | Zucherman et al. | |
| 2008/0015700 A1 | 1/2008 | Zucherman et al. | |
| 2008/0021468 A1 | 1/2008 | Zucherman et al. | |
| 2008/0021560 A1 | 1/2008 | Zucherman et al. | |
| 2008/0021561 A1 | 1/2008 | Zucherman et al. | |
| 2008/0027545 A1 | 1/2008 | Zucherman et al. | |
| 2008/0027552 A1 | 1/2008 | Zucherman et al. | |
| 2008/0027553 A1 | 1/2008 | Zucherman et al. | |
| 2008/0033445 A1 | 2/2008 | Zucherman et al. | |
| 2008/0033553 A1 | 2/2008 | Zucherman et al. | |
| 2008/0033558 A1 | 2/2008 | Zucherman et al. | |
| 2008/0033559 A1 | 2/2008 | Zucherman et al. | |
| 2008/0039853 A1 | 2/2008 | Zucherman et al. | |
| 2008/0039858 A1 | 2/2008 | Zucherman et al. | |
| 2008/0039859 A1 | 2/2008 | Zucherman et al. | |
| 2008/0039945 A1 | 2/2008 | Zucherman et al. | |
| 2008/0039946 A1 | 2/2008 | Zucherman et al. | |
| 2008/0039947 A1 | 2/2008 | Zucherman et al. | |
| 2008/0045958 A1 | 2/2008 | Zucherman et al. | |
| 2008/0045959 A1 | 2/2008 | Zucherman et al. | |
| 2008/0046081 A1 | 2/2008 | Zucherman et al. | |
| 2008/0046085 A1 | 2/2008 | Zucherman et al. | |
| 2008/0046086 A1 | 2/2008 | Zucherman et al. | |
| 2008/0046087 A1 | 2/2008 | Zucherman et al. | |
| 2008/0046088 A1 | 2/2008 | Zucherman et al. | |
| 2008/0051785 A1 | 2/2008 | Zucherman et al. | |
| 2008/0051896 A1 | 2/2008 | Suddaby | |
| 2008/0051898 A1 | 2/2008 | Zucherman et al. | |
| 2008/0051899 A1 | 2/2008 | Zucherman et al. | |
| 2008/0051904 A1 | 2/2008 | Zucherman et al. | |
| 2008/0051905 A1 | 2/2008 | Zucherman et al. | |
| 2008/0058806 A1 | 3/2008 | Klyce et al. | |
| 2008/0058807 A1 | 3/2008 | Klyce et al. | |
| 2008/0058808 A1 | 3/2008 | Klyce et al. | |
| 2008/0058941 A1 | 3/2008 | Zucherman et al. | |
| 2008/0065086 A1 | 3/2008 | Zucherman et al. | |
| 2008/0065212 A1 | 3/2008 | Zucherman et al. | |
| 2008/0065213 A1 | 3/2008 | Zucherman et al. | |
| 2008/0065214 A1 | 3/2008 | Zucherman et al. | |
| 2008/0071280 A1 | 3/2008 | Winslow | |
| 2008/0071378 A1 | 3/2008 | Zucherman et al. | |
| 2008/0071380 A1 | 3/2008 | Sweeney | |
| 2008/0086212 A1 | 4/2008 | Zucherman et al. | |
| 2008/0108990 A1 | 5/2008 | Mitchell | |
| 2008/0114455 A1 | 5/2008 | Lange et al. | |
| 2008/0132952 A1 | 6/2008 | Malandain | |
| 2008/0167655 A1 | 7/2008 | Wang et al. | |
| 2008/0167656 A1 | 7/2008 | Zucherman et al. | |
| 2008/0172057 A1 | 7/2008 | Zucherman et al. | |
| 2008/0177272 A1 | 7/2008 | Zucherman et al. | |
| 2008/0177306 A1 | 7/2008 | Lamborne | |
| 2008/0177312 A1 | 7/2008 | Perez-Cruet et al. | |
| 2008/0183210 A1 | 7/2008 | Zucherman et al. | |
| 2008/0188895 A1 | 8/2008 | Cragg et al. | |
| 2008/0208344 A1 | 8/2008 | Kilpela et al. | |
| 2008/0215058 A1 | 9/2008 | Zucherman et al. | |
| 2008/0221692 A1 | 9/2008 | Zucherman et al. | |
| 2008/0228225 A1 | 9/2008 | Trautwein et al. | |
| 2008/0234708 A1 | 9/2008 | Houser | |
| 2008/0234824 A1 | 9/2008 | Youssef et al. | |
| 2008/0288075 A1 | 11/2008 | Zucherman et al. | |
| 2008/0319550 A1 | 12/2008 | Altarac et al. | |
| 2009/0012528 A1 | 1/2009 | Aschmann et al. | |
| 2009/0118833 A1 | 5/2009 | Hudgins et al. | |
| 2009/0125030 A1 | 5/2009 | Tebbe et al. | |
| 2009/0125036 A1 | 5/2009 | Bleich | |
| 2009/0138046 A1 | 5/2009 | Altarac et al. | |
| 2009/0138055 A1 | 5/2009 | Altarac et al. | |
| 2009/0222043 A1 | 9/2009 | Altarac et al. | |
| 2009/0248079 A1 | 10/2009 | Kwak et al. | |
| 2009/0292315 A1 | 11/2009 | Trieu | |
| 2010/0042217 A1 | 2/2010 | Zucherman et al. | |
| 2010/0082108 A1 | 4/2010 | Zucherman et al. | |
| 2010/0114100 A1 | 5/2010 | Mehdizade | |
| 2010/0131009 A1 | 5/2010 | Roebling | |
| 2010/0160947 A1 | 6/2010 | Akyuz et al. | |
| 2010/0228092 A1 | 9/2010 | Ortiz | |
| 2010/0234889 A1 | 9/2010 | Hess | |
| 2010/0262243 A1 | 10/2010 | Zucherman et al. | |
| 2010/0280551 A1 | 11/2010 | Pool | |
| 2010/0305611 A1 | 12/2010 | Zucherman et al. | |

(56) References Cited

U.S. PATENT DOCUMENTS

| | | |
|---|---|---|
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Lopez |
| 2012/0303039 A1 | 11/2012 | Chin et al. |
| 2012/0330359 A1 | 12/2012 | Kim et al. |
| 2013/0012998 A1 | 1/2013 | Altarac et al. |
| 2013/0072985 A1 | 3/2013 | Kim et al. |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi |
| 2013/0289622 A1 | 10/2013 | Kim |
| 2014/0081332 A1 | 3/2014 | Altarac et al. |
| 2014/0214082 A1 | 7/2014 | Reglos |
| 2015/0150598 A1 | 6/2015 | Tebbe et al. |
| 2015/0150604 A1 | 6/2015 | Kim |
| 2015/0374415 A1 | 12/2015 | Kim |
| 2016/0030092 A1 | 2/2016 | Altarac et al. |
| 2016/0066963 A1 | 3/2016 | Kim |
| 2016/0317193 A1 | 11/2016 | Kim et al. |
| 2017/0071588 A1 | 3/2017 | Choi |
| 2017/0128110 A1 | 5/2017 | Altarac et al. |
| 2017/0245883 A1 | 8/2017 | Tebbe et al. |
| 2017/0258501 A1 | 9/2017 | Altarac et al. |
| 2017/0273722 A1 | 9/2017 | Altarac et al. |
| 2018/0028130 A1 | 2/2018 | Choi |
| 2018/0193064 A1 | 7/2018 | Kim |
| 2018/0228519 A1 | 8/2018 | Altarac et al. |
| 2019/0069933 A1 | 3/2019 | Altarac et al. |
| 2019/0090912 A1 | 3/2019 | Altarac et al. |
| 2019/0105082 A1 | 4/2019 | Altarac et al. |
| 2019/0105083 A1 | 4/2019 | Kim |
| 2019/0201057 A1 | 7/2019 | Altarac et al. |

FOREIGN PATENT DOCUMENTS

| | | |
|---|---|---|
| CN | 101897603 A | 12/2010 |
| DE | 69507480 T2 | 9/1999 |
| EP | 322334 A1 | 6/1989 |
| EP | 0767636 A1 | 4/1997 |
| EP | 0768843 B1 | 2/1999 |
| EP | 1027004 A1 | 8/2000 |
| EP | 1030615 A1 | 8/2000 |
| EP | 1138268 A1 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 0959792 B1 | 11/2007 |
| EP | 1861046 A2 | 12/2007 |
| FR | 2681525 A1 | 3/1993 |
| FR | 2717675 A1 | 3/1994 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO07131165 A2 | 11/1970 |
| WO | WO9404088 A1 | 3/1994 |
| WO | WO9426192 A1 | 11/1994 |
| WO | WO9525485 A1 | 9/1995 |
| WO | WO9531158 A1 | 11/1995 |
| WO | WO9600049 A1 | 1/1996 |
| WO | WO9829047 A1 | 7/1998 |
| WO | WO9921500 A1 | 5/1999 |
| WO | WO9921501 A1 | 5/1999 |
| WO | WO9942051 A1 | 8/1999 |
| WO | WO0013619 A1 | 3/2000 |
| WO | WO0044319 A1 | 8/2000 |
| WO | WO0044321 A2 | 8/2000 |
| WO | WO0128442 A1 | 4/2001 |
| WO | WO0191657 A1 | 12/2001 |
| WO | WO0191658 A1 | 12/2001 |
| WO | WO0203882 A2 | 1/2002 |
| WO | WO0207623 A1 | 1/2002 |
| WO | WO0207624 A1 | 1/2002 |
| WO | WO02051326 A1 | 7/2002 |
| WO | WO02067793 A2 | 9/2002 |
| WO | WO02071960 A1 | 9/2002 |
| WO | WO02076336 A2 | 10/2002 |
| WO | WO03007791 A2 | 1/2003 |
| WO | WO03007829 A1 | 1/2003 |
| WO | WO03008016 A2 | 1/2003 |
| WO | WO03015646 A2 | 2/2003 |
| WO | WO03024298 A2 | 3/2003 |
| WO | WO03045262 A2 | 6/2003 |
| WO | WO03099147 A1 | 12/2003 |
| WO | WO03101350 A1 | 12/2003 |
| WO | WO04073533 A1 | 9/2004 |
| WO | WO04110300 A2 | 12/2004 |
| WO | WO05009300 A1 | 2/2005 |
| WO | WO05013839 A2 | 2/2005 |
| WO | WO05025461 A2 | 3/2005 |
| WO | WO05041799 A1 | 5/2005 |
| WO | WO05044152 A1 | 5/2005 |
| WO | WO05055868 A2 | 6/2005 |
| WO | WO05079672 A2 | 9/2005 |
| WO | WO2005086776 A2 | 9/2005 |
| WO | WO05115261 A1 | 12/2005 |
| WO | WO06033659 A2 | 3/2006 |
| WO | WO06034423 A2 | 3/2006 |
| WO | WO06039243 A1 | 4/2006 |
| WO | WO06039260 A2 | 4/2006 |
| WO | WO06045094 A2 | 4/2006 |
| WO | WO2006045094 A2 | 4/2006 |
| WO | WO06063047 A2 | 6/2006 |
| WO | WO06065774 A1 | 6/2006 |
| WO | WO2006063047 A2 | 6/2006 |
| WO | WO2006064356 A1 | 6/2006 |
| WO | WO2006089085 A2 | 8/2006 |
| WO | WO06102269 A2 | 9/2006 |
| WO | WO06102428 A1 | 9/2006 |
| WO | WO06102485 A2 | 9/2006 |
| WO | WO06107539 A1 | 10/2006 |
| WO | WO06110462 A2 | 10/2006 |
| WO | WO06110464 A1 | 10/2006 |
| WO | WO06110767 A1 | 10/2006 |
| WO | WO06113080 A2 | 10/2006 |
| WO | WO06113406 A2 | 10/2006 |
| WO | WO06113814 A2 | 10/2006 |
| WO | WO06118945 A1 | 11/2006 |
| WO | WO06119235 A1 | 11/2006 |
| WO | WO06119236 A2 | 11/2006 |
| WO | WO06135511 A1 | 12/2006 |
| WO | WO07015028 A1 | 2/2007 |
| WO | WO07035120 A1 | 3/2007 |
| WO | WO07075375 A2 | 7/2007 |
| WO | WO07075788 A2 | 7/2007 |
| WO | WO07075791 A2 | 7/2007 |
| WO | WO07089605 A2 | 8/2007 |
| WO | WO07089905 A2 | 8/2007 |
| WO | WO07089975 A1 | 8/2007 |
| WO | WO07097735 A2 | 8/2007 |
| WO | WO07109402 A2 | 9/2007 |
| WO | WO07110604 A1 | 10/2007 |
| WO | WO07111795 A1 | 10/2007 |
| WO | WO07111979 A2 | 10/2007 |
| WO | WO07111999 A2 | 10/2007 |
| WO | WO07117882 A1 | 10/2007 |
| WO | WO07121070 A2 | 10/2007 |
| WO | WO07127550 A2 | 11/2007 |
| WO | WO07127588 A1 | 11/2007 |
| WO | WO07127677 A1 | 11/2007 |
| WO | WO07127689 A2 | 11/2007 |
| WO | WO07127694 A2 | 11/2007 |

(56) References Cited

FOREIGN PATENT DOCUMENTS

| WO | WO07127734 A2 | 11/2007 |
|---|---|---|
| WO | WO07127736 A2 | 11/2007 |
| WO | WO07134113 A2 | 11/2007 |
| WO | WO2008009049 A1 | 1/2008 |
| WO | WO08048645 A2 | 4/2008 |
| WO | WO2008057506 A2 | 5/2008 |
| WO | WO2008130564 A1 | 10/2008 |
| WO | WO2009014728 A2 | 1/2009 |
| WO | WO2009033093 A1 | 3/2009 |
| WO | WO2009086010 A2 | 7/2009 |
| WO | WO2009091922 A2 | 7/2009 |
| WO | WO2009094463 A2 | 7/2009 |
| WO | WO2009114479 A2 | 9/2009 |
| WO | WO2011084477 A2 | 7/2011 |
| WO | WO2015171814 A1 | 11/2015 |

OTHER PUBLICATIONS

Australia Exam Report for Application No. AU2006329867, Applicant: The Board of Trustees of Leland Stanford Junior University; Date of Issue: Jan. 27, 2012, 2 pages.
Australia Exam Report for Application No. AU2007317886, Applicant: VertiFlex, Inc.; Date of Issue: Jun. 18, 2012, 3 pages.
Australia Exam Report for Application No. AU2008241447, Applicant: VertiFlex, Inc.; Date of Issue: Jul. 5, 2012, 4 pages.
Australia Exam Report for Application No. AU2008275708, Applicant: VertiFlex, Inc.; Date of Issue: Nov. 12, 2012, 4 pages.
Australia Exam Report for Application No. AU2008279680, Applicant: VertiFlex, Inc.; Date of Issue: Oct. 30, 2012, 5 pages.
Australia Exam Report for Application No. AU2008296066, Applicant: VertiFlex, Inc.; Date of Issue: Mar. 6, 2013, 3 pages.
Australia Exam Report for Application No. AU2008343092, Applicant: VertiFlex, Inc.; Date of Issue: Feb. 8, 2013, 4 pages.
Australia Exam Report for Application No. AU2013273815, Applicant: The Board of Trustees of Leland Stanford Junior University; Date of Issue: Apr. 17, 2015, 3 pages.
Australia Exam Report for Application No. AU2014203394, Applicant: VertiFlex, Inc., Date of Issue: Mar. 15, 2016, 2 pages.
Australia Exam Report No. 1 for Application No. AU2009206098, Applicant: VertiFlex, Inc.; Date of Issue: Mar. 6, 2013, 4 pages.
Australia Exam Report No. 2 for Application No. AU2009206098, Applicant: VertiFlex, Inc.; Date of Issue: Aug. 19, 2014, 4 pages.
Canada Exam Report for Application No. CA2634251, Applicant: The Board of Trustees of Leland Stanford Junior University; Date of Issue: Dec. 3, 2013, 2 pages.
Canada Exam Report for Application No. CA2668833, Applicant: Vertiflex, Inc.; Date of Issue: Dec. 5, 2013, 2 pages.
Canada Exam Report for Application No. CA2695937, Applicant: Vertiflex, Inc.; Date of Issue: Aug. 7, 2014, 2 pages.
Canada Exam Report for Application No. CA2697628, Applicant: Vertiflex, Inc.; Date of Issue: Oct. 16, 2014, 2 pages.
Canada Exam Report for Application No. CA2698718, Applicant: Vertiflex, Inc.; Date of Issue: May 20, 2014, 3 pages.
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
Decision on Petition in U.S. Appl. No. 60/592,099, filed May 4, 2005.
European Further Exam Report for Application No. EP09702116.6; Applicant: VertiFlex, Inc.; Date of Mailing: Jul. 4, 2016, 4 pages.
European Examination Report for Application No. 08794704.0; Applicant: Vertiflex, Inc.; Date of Mailing Apr. 5, 2017, 6 pages.
European Examination Report for Application No. 08799267.3; Applicant: Vertiflex, Inc.: Date of Mailing Sep. 5, 2017, 4 pages.
Fast, Avital et al., "Surgical Treatment of Lumbar Spinal Stenosis in the Elderly," Arch Phys. Med Rehabil., Mar. 1985, pp. 149-151, vol. 66.

First Examination Report in European Patent Application No. 08780034.8, mail date Jan. 16, 2017, 5 pages.
Further Examination Report in European Patent Application No. 07861426.0, mail date Oct. 4, 2017, 4 pages.
Further Examination Report in European Patent Application No. 08867282.9, mail date Oct. 15, 2018, 7 pages.
International Search Report and Written Opinion; Application No. PCT/US2006/047824; Mailing Date: Oct. 16, 2008, 17 pages.
International Search Report and Written Opinion; Application No. PCT/US2006/048611; Mailing Date: Oct. 14, 2008; 10 pages.
International Search Report and Written Opinion; Application No. PCT/US2006/048614; Mailing Date: Feb. 3, 2006; 23 pages.
International Search Report and Written Opinion; Application No. PCT/US2007/022171; Mailing Date: Apr. 15, 2008, 9 pages.
International Search Report and Written Opinion; Application No. PCT/US2007/023312; Mailing Date: May 22, 2008, 14 pages.
International Search Report and Written Opinion; Application No. PCT/US2008/004901; Mailing Date: Aug. 19, 2008, 7 pages.
International Search Report and Written Opinion; Application No. PCT/US2008/008382; Mailing Date: Mar. 2, 2009, 13 pages.
International Search Report and Written Opinion; Application No. PCT/US2008/008983; Mailing Date: Feb. 23, 2009, 7 pages.
International Search Report and Written Opinion; Application No. PCT/US2008/075487; Mailing Date: Dec. 31, 2008, 7 pages.
International Search Report and Written Opinion; Application No. PCT/US2008/087527; Mailing Date: Jul. 30, 2009, 10 pages.
International Search Report and Written Opinion; Application No. PCT/US2009/031150; Mailing Date: Aug. 28, 2009, 6 pages.
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
McCulloch, John A., Young, Paul H., "Essentials of Spinal Microsurgery," 1998, pp. 453-485. Lippincott-Raven Publishers, Philadelphia, PA (37 pages total).
Minns, R.J., et al., "Preliminary Design and Experimental Studies of a Noval Soft Implant for Correcting Sagittal Plane Instability in the Lumbar Spine," (1997) Spine, 22(16): 1819-1827.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
Supplementary European Search Report for Application No. EP06845480; Applicant: VertiFlex, Inc.; Date of Completion: Aug. 14, 2012, 9 pages.
Supplementary European Search Report for Application No. EP07861426; Applicant: VertiFlex, Inc.; Date of Issue: Jun. 7, 2011, 6 pages.
Supplementary European Search Report for Application No. EP07861721.4; Applicant: VertiFlex, Inc.; Date of Issue: Nov. 24, 2009, 6 pages.
Supplementary European Search Report for Application No. EP08742949.4; Applicant: VertiFlex, Inc.; Date of Issue: Jul. 19, 2012, 4 pages.
Supplementary European Search Report for Application No. EP08780034.8; Applicant: VertiFlex, Inc.; Date of Issue: Sep. 19, 2012, 7 pages.
Supplementary European Search Report for Application No. EP08794704.0; Applicant: VertiFlex, Inc.; Date of Issue: Oct. 23, 2012, 9 pages.
Supplementary European Search Report for Application No. EP08799267.3; Applicant: VertiFlex, Inc.; Date of Issue: Jun. 29, 2011, 7 pages.
Supplementary European Search Report for Application No. EP08867282.9; Applicant: VertiFlex, Inc.; Date of Issue: Nov. 28, 2012, 10 pages.
Supplementary European Search Report for Application No. EP09170304.1; Applicant: VertiFlex, Inc.; Date of Issue: Nov. 24, 2009, 5 pages.

(56) References Cited

OTHER PUBLICATIONS

Supplementary European Search Report for Application No. EP09170338.9; Applicant: VertiFlex, Inc.; Date of Issue: Nov. 24, 2009, 6 pages.
Supplementary European Search Report for Application No. EP09702116.6; Applicant: VertiFlex, Inc.; Date of Issue: Feb. 11, 2011, 7 pages.
Supplementary European Search Report for Application No. EP11151901.3; Applicant: VertiFlex, Inc.; Date of Issue: Apr. 7, 2011, 6 pages.
Supplementary European Search Report for Application No. EP13184922.6; Applicant: VertiFlex, Inc.; Date of Issue: Oct. 30, 2013, 8 pages.
Supplementary European Search Report; Application No. EP07861426.0; Applicant: Vertiflex, Inc.; Date of Completion: Jun. 7, 2011, 6 pages.
Supplementary European Search Report; Application No. EP07861721.4; Applicant: Vertiflex, Inc.; Date of Completion: Nov. 24, 2009, 6 pages.
Supplementary European Search Report; Application No. EP09170304.1; Applicant: Vertiflex, Inc.; Date of Completion: Nov. 11, 2009, 5 pages.
Supplementary European Search Report; Application No. EP09170338.9; Applicant: Vertiflex, Inc.; Date of Completion: Nov. 12, 2009, 6 pages.
Supplementary European Search Report; Application No. EP09702116.6; Applicant: Vertiflex, Inc.; Date of Completion: Feb. 11, 2011, 6 pages.
Supplementary European Search Report; Application No. EP11151901.3; Applicant: Vertiflex, Inc.; Date of Completion: Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.
Tredway, Trent L et al., "Minimally Invasive Transforaminal Lumbar Interbody Fusion (MI-TLIF) and Lateral Mass Fusion with the MetRx System," (14 pages total), 2005.
Vaccaro, Alexander J. et al., MasterCases Spine Surgery, 2001, pp. 100-107. Thieme Medical Publishers, Inc., NY. (10 pages total).
Vertos mild Devices Kit—PRT-00430-C—Instructions for Use (13 pages total); see http://vertosmed.com/docs/mild1FU_PRT-00430-C.pdf., 2012.
Official Communication for U.S. Appl. No. 18/082,509 mailed Sep. 21, 2023.

* cited by examiner

SECTION A-A

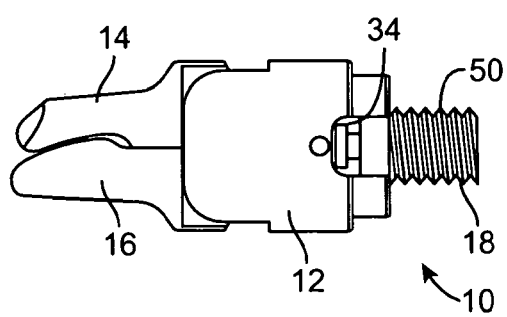
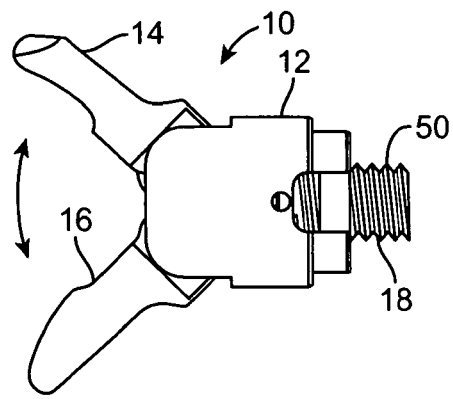
FIG. 5a          FIG. 5b
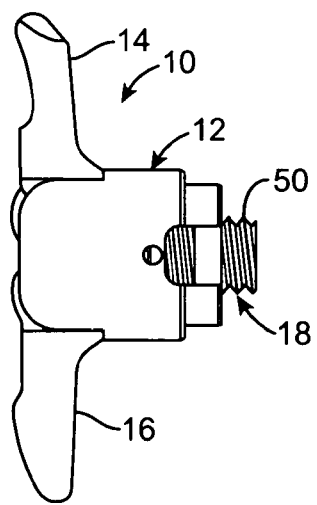
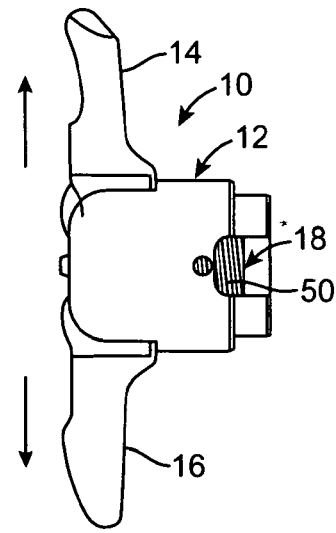
FIG. 5c          FIG. 5d

SECTION A-A

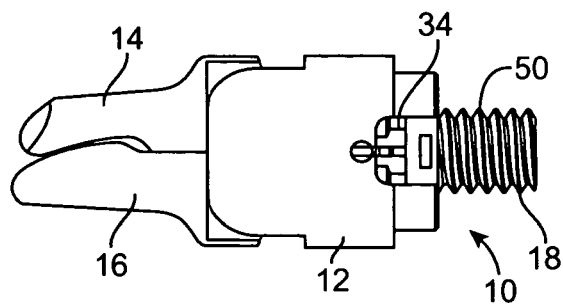
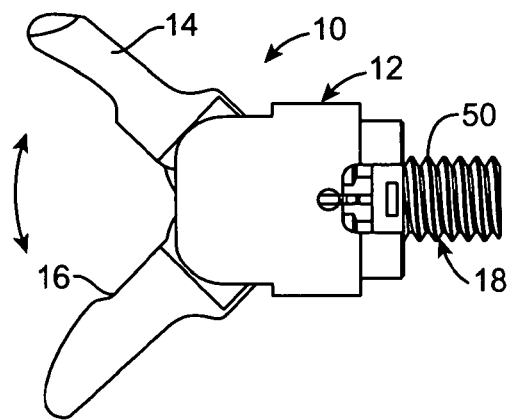
FIG. 12a          FIG. 12b
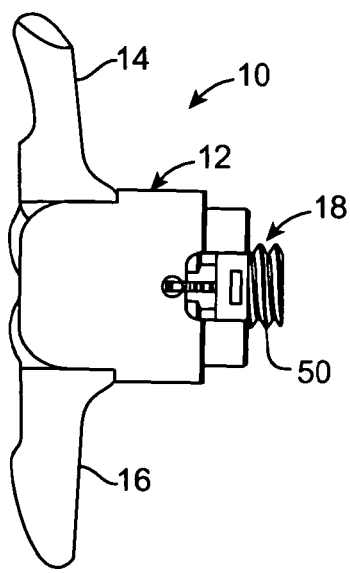
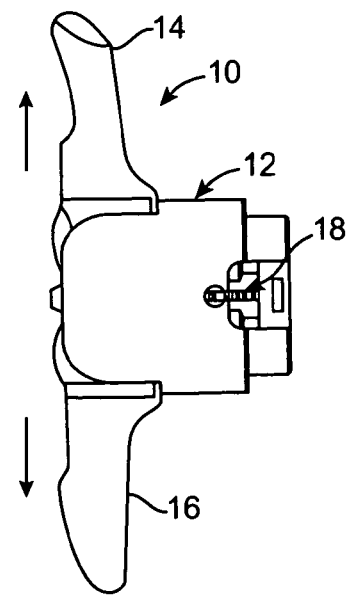
FIG. 12c          FIG. 12d

INTERSPINOUS SPACER

CROSS-REFERENCE TO RELATED APPLICATIONS

This application is a continuation-in-part of U.S. patent application Ser. No. 17/522,350 entitled "Interspinous Spacer" filed on Nov. 9, 2021, which is a continuation of U.S. patent application Ser. No. 15/966,287 filed on Apr. 30, 2018, now U.S. Pat. No. 11,229,461, which is a continuation of U.S. patent application Ser. No. 14/887,201 filed on Oct. 19, 2015, now U.S. Pat. No. 9,956,011, which is a continuation of U.S. patent application Ser. No. 13/619,195 filed on Sep. 14, 2012, now U.S. Pat. No. 9,161,783, which is a continuation of U.S. patent application Ser. No. 12/220,427 filed on Jul. 24, 2008, now U.S. Pat. No. 8,277,488, which is a continuation-in-part of U.S. patent application Ser. No. 12/217,662 filed on Jul. 8, 2008, now U.S. Pat. No. 8,273,108, which is a continuation-in-part of U.S. patent application Ser. No. 12/148,104 filed on Apr. 16, 2008, now U.S. Pat. No. 8,292,922. U.S. patent application Ser. No. 12/220,427 is also a continuation-in-part of U.S. patent application Ser. No. 11/593,995 filed on Nov. 7, 2006, now U.S. Pat. No. 8,425,559, which is a continuation-in-part of U.S. patent application Ser. No. 11/582,874 filed on Oct. 18, 2006, now U.S. Pat. No. 8,128,662.

Other related patent applications, which are not claimed as priority patent applications, include U.S. patent application Ser. No. 11/314,712 filed on Dec. 20, 2005, now U.S. Pat. No. 8,152,837, which is a continuation-in-part of U.S. patent application Ser. No. 11/190,496 filed on Jul. 26, 2005, now U.S. Pat. No. 8,409,282, which is a continuation-in-part of U.S. patent application Ser. No. 11/079,006 filed on Mar. 10, 2005, now U.S. Pat. No. 8,012,207, which is a continuation-in-part of U.S. patent application Ser. No. 11/052,002 filed on Feb. 4, 2005, now U.S. Pat. No. 8,317,864, which is a continuation-in-part of U.S. patent application Ser. No. 11/006,502 filed on Dec. 6, 2004, now U.S. Pat. No. 8,123,807, which is a continuation-in-part of U.S. patent application Ser. No. 10/970,843 filed on Oct. 20, 2004, now U.S. Pat. No. 8,167,944, all of which are hereby incorporated by reference in their entireties. U.S. patent application Ser. No. 12/220,427 also claims priority to and the benefit of U.S. Provisional Patent Application No. 60/961,741 filed on Jul. 24, 2007. U.S. patent application Ser. No. 12/217,662 also claims priority to and the benefit of U.S. Provisional Application No. 60/958,876. U.S. patent application Ser. No. 12/148,104 also claims priority to and the benefit of U.S. Provisional Patent Application No. 60/923,971 filed on Apr. 17, 2007, and U.S. Provisional Patent Application No. 60/923,841 entitled filed on Apr. 16, 2007.

All of the above applications and patents are hereby incorporated by reference in their entireties.

FIELD

The present invention generally relates to medical devices, in particular, implants for placement between adjacent spinous processes of a patient's spine.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down—all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent interspinous processes of a patient's spine. The implanted spacer opens the spinal canal, maintains the desired distance between vertebral body segments, and as a result, avoids impingement of nerves and relieves pain. For suitable candidates, an implantable interspinous spacer may provide significant benefits in terms of pain relief.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are generally preferred as they affect less tissue and result in speedier recovery times. As such, there is a need for interspinous spacers that work well with surgical techniques that are minimally invasive for the patient. The present invention sets forth such a spacer.

SUMMARY

According to one aspect of the invention, an implantable spacer for placement between adjacent spinous processes is disclosed. The implant includes a body defining a longitudinal axis and passageway through at least a portion of the body. A first arm and a second arm are both connected to the body and capable of rotation with respect to the body. Each arm defines a configuration suitable for cradling a spinous process. Each arm has a proximal caming surface. The spacer further includes an actuator assembly connected to the body. The actuator assembly comprises an actuator having at least one bearing surface and a threaded shaft connected to the actuator and configured for movement with respect to the body. The actuator assembly is configured such that the actuator is disposed inside the body and configured to move relative to the body such that the at least one bearing surface contacts the caming surfaces of the arms to thereby rotate the arms from an undeployed configuration in which the arms are substantially parallel to the longitudinal axis of the body to a deployed configuration in which the arms are substantially perpendicular to the longitudinal axis of the body. The arms seat adjacent spinous processes when in the deployed configuration.

According to another aspect of the invention, an implantable spacer for placement between adjacent spinous processes is disclosed. The spacer includes a body defining a longitudinal axis and passageway through at least a portion of the body. At least a first arm is connected to the body and capable of movement with respect to the body and configured for receiving a spinous process. The spacer further includes an actuator connected to the body, disposed inside the longitudinal passageway and configured to move relative to the body to deploy the at least first arm from an undeployed configuration in which the first arm is substantially parallel to the longitudinal axis of the body to at least one deployed configuration in which the first arm is substantially perpendicular to the longitudinal axis of the body. The first arm receives a spinous process when in the at least one deployed configuration.

According to another aspect of the invention, an implantable spacer for placement between adjacent spinous processes is disclosed. The spacer includes a body defining a longitudinal axis and passageway through at least a portion of the body. A first arm and a second arm are connected to the body and capable of rotation with respect to the body. Each arm has a pair of extensions and a saddle defining a configuration for seating a spinous process therein. Each arm has a proximal caming surface. The spacer further includes an actuator connected to the body and configured to move relative to the body to deploy the arms from an undeployed configuration in which the arms are substantially parallel to the longitudinal axis of the body to a deployed configuration in which the arms are substantially perpendicular to the longitudinal axis of the body. The arms seat adjacent spinous processes when in the deployed configuration. The spacer further includes a retainer configured to retain the actuator inside the body while permitting the actuator relative movement with respect to the body.

According to another aspect of the invention, an implantable spacer for placement between a superior spinous process and an adjacent inferior spinous process is disclosed. The spacer includes a body defining a longitudinal axis and passageway through at least a portion of the body. At least a first arm is connected to the body and capable of movement with respect to the body. The first arm has a configuration for seating the superior spinous process. The spacer further includes an actuator connected to the body, disposed inside the longitudinal passageway and configured to move relative to the body to deploy the at least first arm from an undeployed configuration in which the first arm is substantially parallel to the longitudinal axis of the body to at least one deployed configuration in which the first arm is substantially perpendicular to the longitudinal axis of the body. The first arm seats the superior spinous process when in the at least one deployed configuration.

According to another aspect of the invention, a method for implanting an interspinous spacer into a patient is disclosed. The method includes the step of providing an implantable spacer configured for placement between adjacent spinous processes. The spacer includes a body having a longitudinal axis. The spacer further includes at least a first arm connected to the body and capable of movement with respect to the body and configured for receiving a spinous process. The spacer further includes an actuator connected to the body and configured to move relative to the body to deploy the at least first arm from an undeployed configuration in which the first arm is substantially parallel to the longitudinal axis of the body to at least one deployed configuration in which the first arm is substantially perpendicular to the longitudinal axis of the body. The first arm receives a spinous process when in the at least one deployed configuration. An incision is created in the patient. The spacer is inserted through the incision to a targeted interspinous process space between adjacent spinous processes. The actuator is moved to move the at least first arm from an undeployed configuration to a first deployed configuration. The actuator is moved to move the at least first arm from the first deployed configuration to a second deployed configuration.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 5a illustrates a side view of a spacer in a closed, undeployed configuration according to the present invention.

FIG. 5b illustrates a side view of a spacer in a partially deployed configuration according to the present invention.

FIG. 5c illustrates a side view of a spacer in a deployed configuration according to the present invention.

FIG. 5d illustrates a side view of a spacer in a deployed and extended configuration according to the present invention.

FIG. 12a illustrates a side view of a spacer in a closed, undeployed configuration according to the present invention.

FIG. 12b illustrates a side view of a spacer in a partially deployed configuration according to the present invention.

FIG. 12c illustrates a side view of a spacer in a deployed configuration according to the present invention.

FIG. 12d illustrates a side view of a spacer in a deployed and extended configuration according to the present invention.

DETAILED DESCRIPTION

Figure 1A:
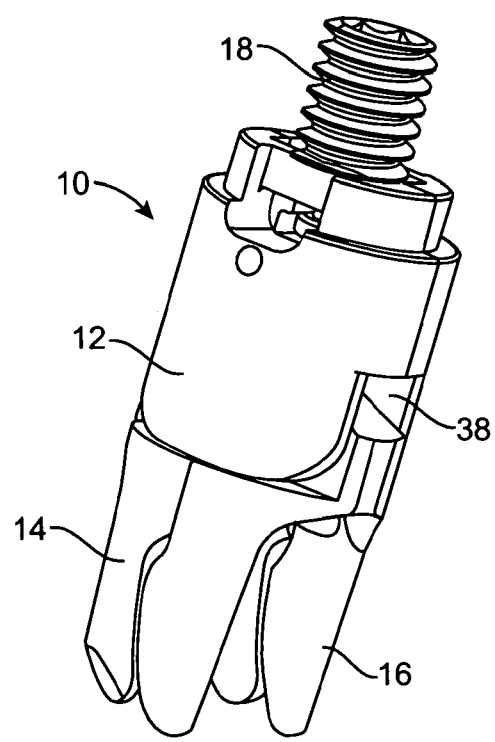
FIG. 1a illustrates a perspective view of a spacer according to the present invention.

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a spinal segment" may include a plurality of such spinal segments and reference to "the screw" includes reference to one or more screws and equivalents thereof known to those skilled in the art, and so forth.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention is described in the accompanying figures and text as understood by a person having ordinary skill in the field of spinal implants and implant delivery instrumentation.

With reference to FIGS. 1a-1f, various views of a spacer 10 according to the present invention are shown. The spacer 10 includes a body 12 connected to a superior extension member or arm 14, an inferior extension member or arm 16, and an actuator assembly 18.

Turning now to FIGS. 2a-2d, the body 12 will now be described. The body 12 is shown to have a clamshell construction with a left body piece 20 (shown in FIGS. 2a and 2b) joined to a right body piece 22 (shown in FIGS. 2c and 2d) to capture arms 14, 16 inside. With the right and left body pieces 20, 22 joined together, the body 12 is generally cylindrical. It has a cross-sectional size and shape that allows for implantation between adjacent spinous processes and facilitates delivery into a patient through a narrow port or cannula.

The inside of the body 12 defines an arm receiving portion 24 and an actuator assembly receiving portion 26 with features formed in each of the left and right body pieces 20, 22 that together define the arm and actuator assembly receiving portions 24, 26. In one variation, the arm receiving portion 24 includes slots or openings 28 that receive pins formed on the arms 14, 16 such that the pins rotate and/or translate inside the openings 28. The actuator assembly receiving portion 26 includes a threaded passageway 30. Other features include a tongue and groove for mating with the opposite clamshell.

Figure 1B:
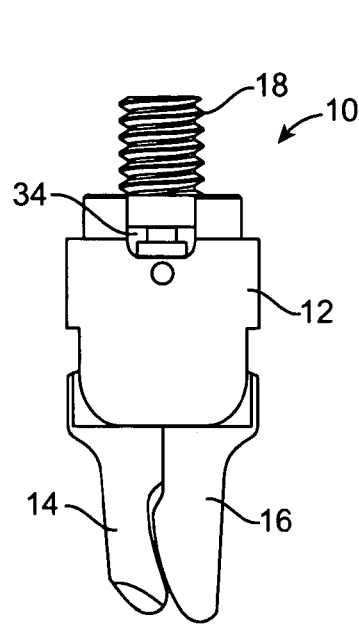
FIG. 1b illustrates a side view of a spacer according to the present invention.
Figure 1C:
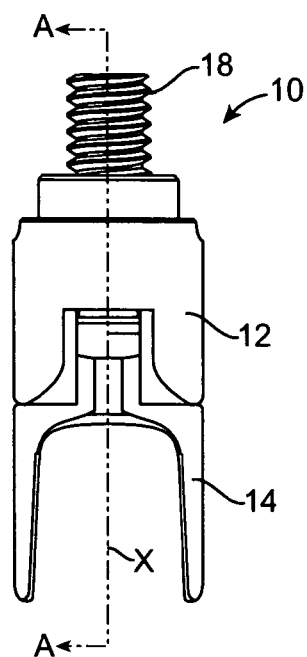
FIG. 1c illustrates a top view of a spacer according to the present invention.
Figure 1D:
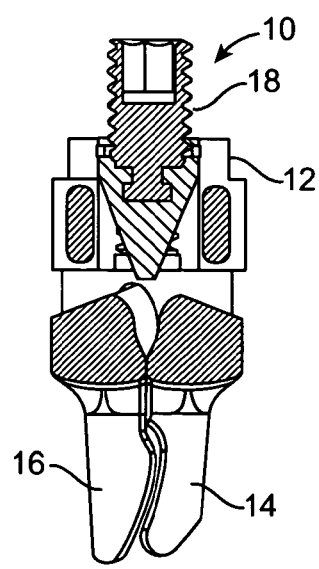
FIG. 1d illustrates a cross-sectional view of the spacer of FIG. 1c taken along line A-A according to the present invention.
Figure 1E:
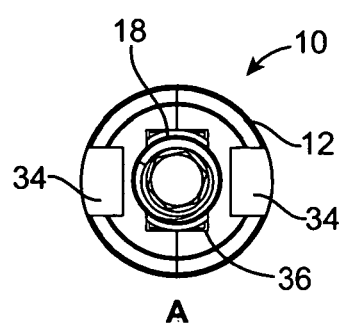
FIG. 1e illustrates an end view of a spacer according to the present invention.

The outside of the body 12 defines a ledge 32 along at least a portion of the periphery. Notches 34 are formed at opposite locations as also shown in FIG. 1B. The notches 34 are configured for pronged attachment to a spacer delivery instrument. When joined together, the left and right body pieces 20, 22 define a proximal opening 36 (as seen in FIG. 1e) and a distal opening 38 (as seen in FIG. 1a) in the body 12. A longitudinal scallop (not shown) extending from the proximal end of the spacer to the distal end is formed in the outer surface of the body 12 to facilitate placement of the spacer 10 between and to conform to the anatomy of adjacent interspinous processes.

Figure 3A:
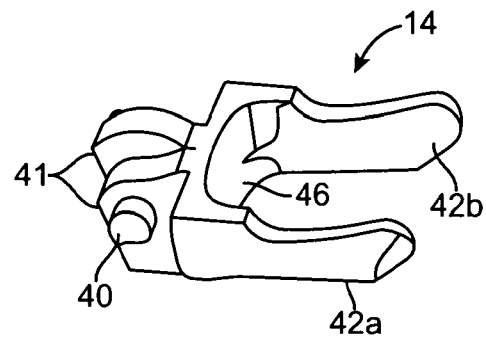
FIG. 3a illustrates a perspective view of a superior arm of a spacer according to the present invention.
Figure 3B:
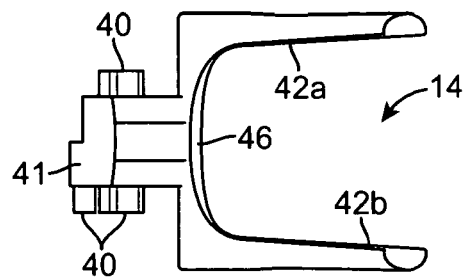
FIG. 3b illustrates a back view of a superior arm of a spacer according to the present invention.
Figure 3C:
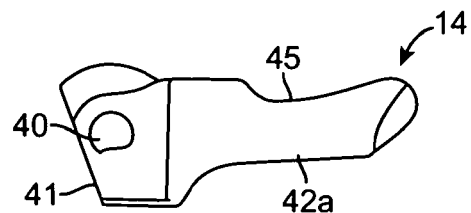
FIG. 3c illustrates a side view of a superior arm of a spacer according to the present invention.
Figure 3D:
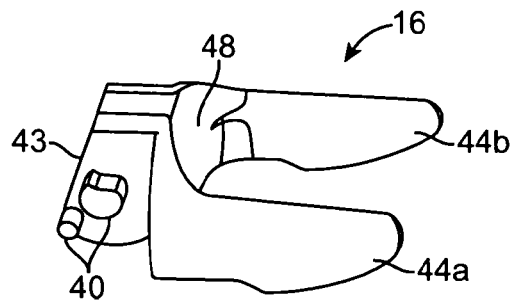
FIG. 3d illustrates a perspective view of an inferior arm of a spacer according to the present invention.
Figure 3E:
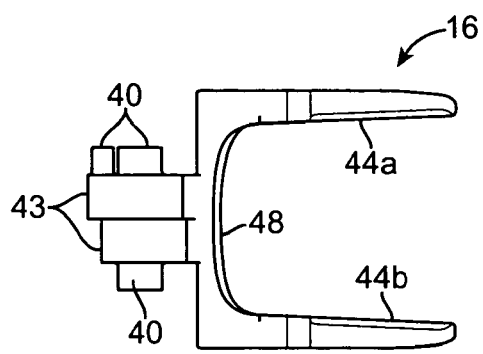
FIG. 3e illustrates a back view of an inferior arm of a spacer according to the present invention.
Figure 3F:
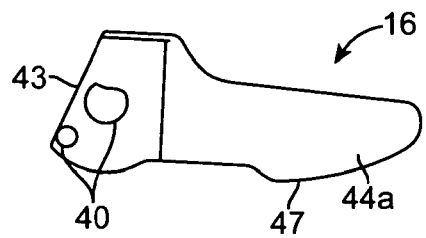
FIG. 3f illustrates a side view of an inferior arm of a spacer according to the present invention.

Turning now to FIGS. 3a-3c, the superior arm 14 is shown and in FIGS. 3d-3f, the inferior arm 16 is shown. The superior and inferior arms 14, 16 include pins 40 for mating with the body 12, in particular, for mating with the slots/openings 28 of the arm receiving portion 24. Each of the superior and inferior arms 14, 16 includes at least one caming surface 41, 43, respectively, for contact with the actuator assembly 18. The superior and inferior arms 14, 16 include elongated superior extensions 42a, 42b and elongated inferior extensions 44a, 44b, respectively. Extensions 42a and 44a are located on the left adjacent to the left body piece 20 and extensions 42b and 44b are located on right adjacent to the right body piece 22. Superior extensions 42a, 42b extend substantially parallel to each other in both an undeployed configuration and in a deployed configuration as do inferior extensions 44a, 44b. Extending between extensions 42a, 42b is a strut, bridge, bracket or saddle 46 that forms a superior substantially U-shaped configuration that is sized and configured to receive a superior spinous process. As seen in FIG. 3c, the anterior face of the superior extensions 14 includes a slight concavity or curvature 45 for conforming to the bony anatomy of the superior spinous process and or lamina. Also, extending between inferior extensions 44a, 44b is a strut, bridge, bracket or saddle 48 that forms an inferior substantially U-shaped configuration together with the extensions 44a, 44b that is sized and configured to receive an inferior spinous process of a spinal motion segment. As seen in FIG. 3f, the anterior face of the inferior extensions 16 includes a slight convexity or curvature 47 for conforming to the bony anatomy of the inferior spinous process and/or lamina.

The superior and inferior arms 14, 16 are movably or rotatably connected to the body 12, for example by hinge means or the like to provide rotational movement from an undeployed configuration to a deployed configuration that arcs through about a 90 degree range or more with respect to the body 12. The arms 14, 16 are rotationally movable between at least an undeployed, collapsed or folded state (as shown in FIGS. 1a-1e) and at least one deployed state (as shown in FIGS. 5c, 5d, 6b, 6c, 7b, and 7c). In the undeployed state, the arm pairs 14, 16 are aligned generally or substantially axially (i.e., axially with the longitudinal axis, defined by the body 12 or to the translation path into the interspinous space of the patient) to provide a minimal lateral or radial profile. The longitudinal axis X of the spacer and body is shown in FIG. 1c. In the deployed state, the arm pairs 14, 16 are positioned such that each of the U-shaped saddles are in a plane (or planes) or have a U-shaped projection in a plane that is (are) generally or substantially transverse to the longitudinal axis X defined by the body 12 or to the collapsed position or to the implantation path into the interspinous space of the patient. In one variation, the spacer 10 is configured such the arms 14, 16 are linearly moveable or translatable within the plane from a first deployed state (such as the state shown in FIGS. 5c, 6b and 7b) to and from a second deployed state (such as the state shown in FIGS. 5d, 6c and 7c) characterized by an additional translation of at least one of the arms 14, 16 with respect to the body 12 along a direction of the arrows as shown in FIG. 7c. More specifically, the arms 14, 16 can be extended in the general vertical direction along an axis along the general length the spine wherein the arms 14, 16 are extended away from each other and away from the body 12 as denoted by the arrows in FIG. 7c. This feature advantageously allows for the most minimally invasive configuration for the spacer without compromising the ability of the spacer 10 to seat and contain the spinous processes in between levels where the anatomy of the spinous processes is such that the interspinous process space increases in the anterior direction or without compromising the ability of the spacer to provide adequate distraction. The arms 14, 16 are connected to the body 12 and/or to each other in a manner that enables them to be moved simultaneously or independently of each other, as well as in a manner that provides passive deployment and/or vertical extension or, alternatively, active or actuated deployment and/or vertical extension.

Turning back to FIG. 1f, the actuator assembly 18 will now be described. The actuator assembly 18 includes an actuator 48 connected to a shaft 50 and retainer 52. The actuator 48 includes a distal end 54 and a proximal end 56 and at least two bearing surfaces 58. The bearing surfaces 58 angle towards each other from the proximal end 54 to the distal end 56. The proximal end 54 of the actuator 48 includes a shaft receiving portion 60 configured to receive the shaft 50. The distal end of the actuator 48 is further configured to engage the superior and inferior arms 14, 16 such that forward translation of the actuator 48 relative to the body 12 effects deployment of the arms into at least one deployed configuration.

Figure 1F:
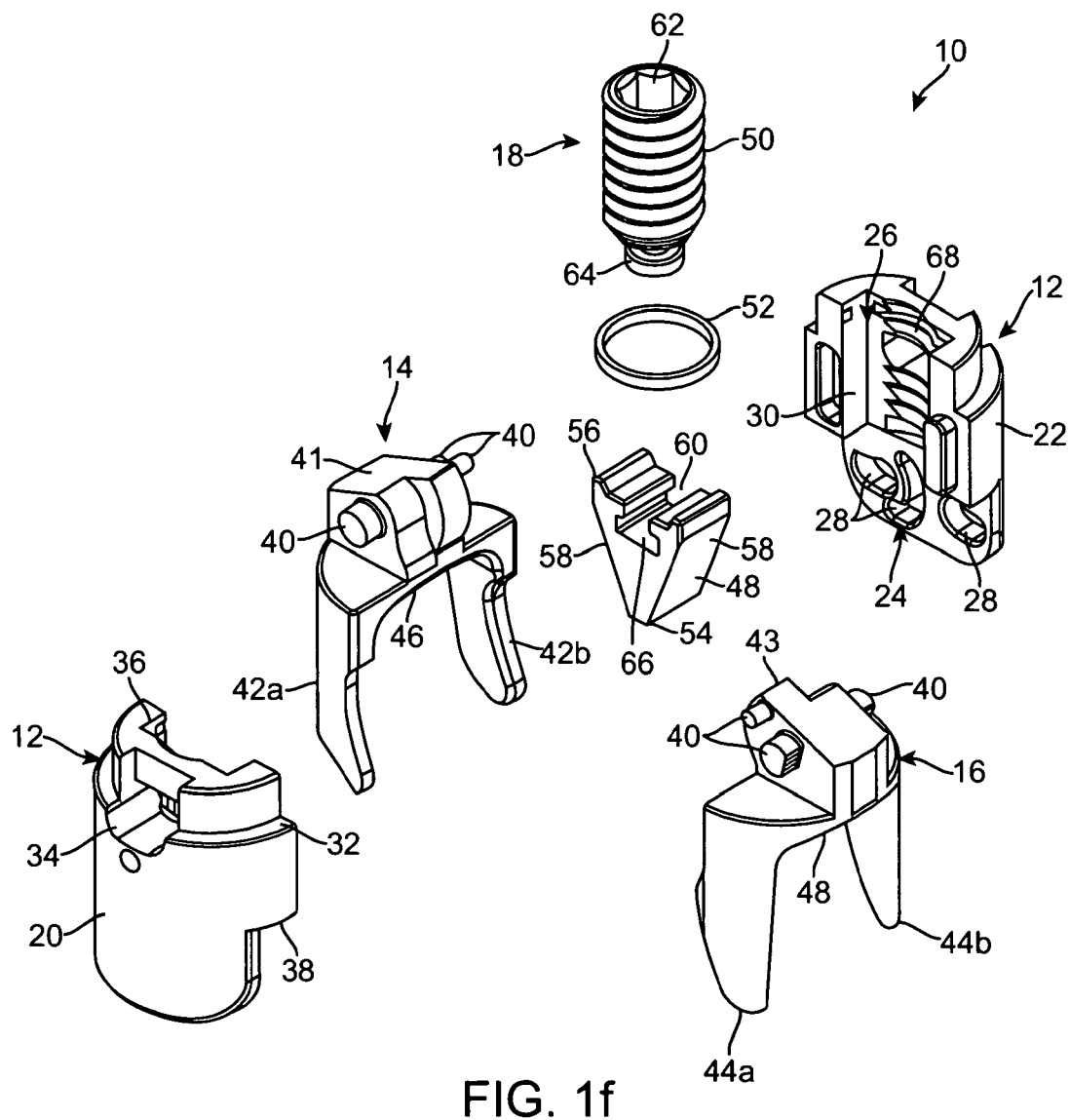
FIG. 1f illustrates an exploded perspective view of a spacer according to the present invention.
Figure 2A:
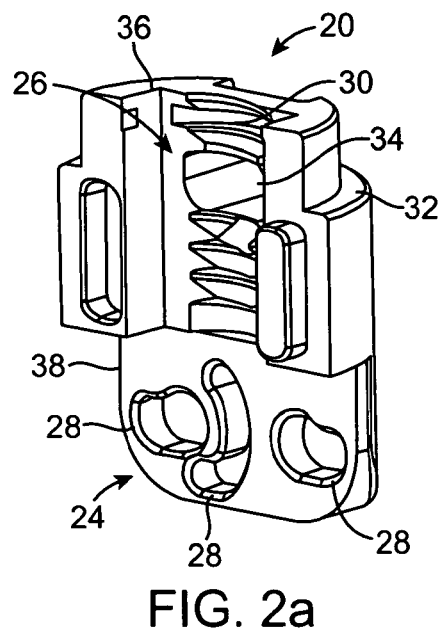
FIG. 2a illustrates a perspective view of half of a body of a spacer according to the present invention.
Figure 2B:
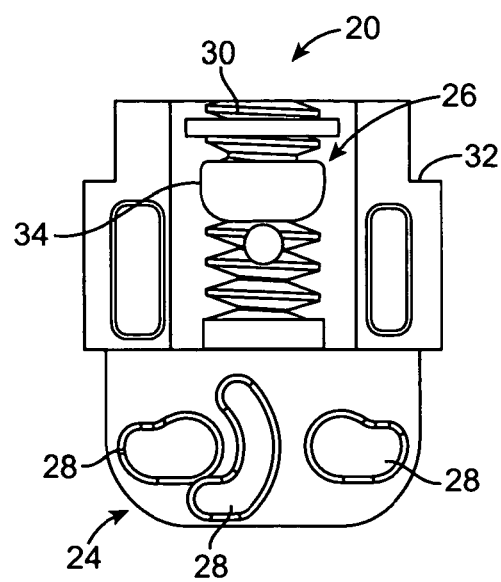
FIG. 2b illustrates a side view of half of a body of a spacer according to the present invention.
Figure 2C:
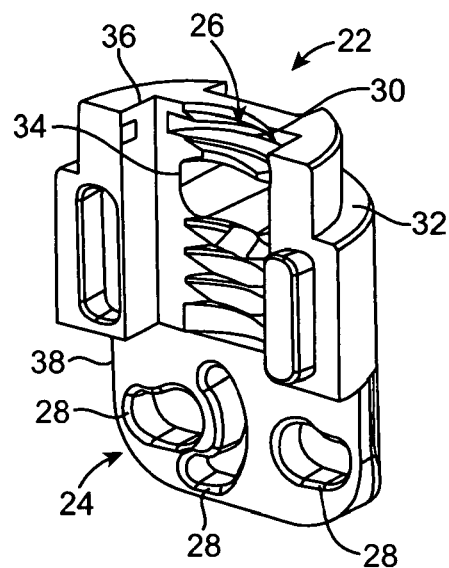
FIG. 2c illustrates a perspective view of another half of a body of a spacer according to the present invention.
Figure 2D:
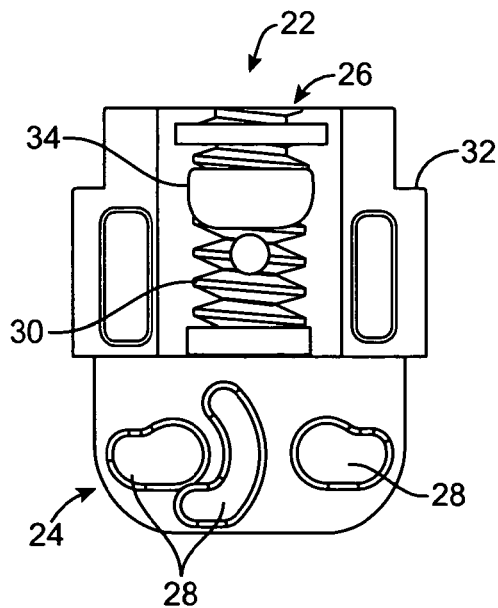
FIG. 2d illustrates a side view of the other half of a body of a spacer according to the present invention.

Still referencing FIG. 1f, the shaft 50 is substantially cylindrical in shape and includes a threaded outer surface for engagement with the threaded inner surface of the actuator assembly receiving portion 26 of the body 12. The threads on the inner surface of the body 12 are formed by the conjunction of both left and right body pieces 20, 22. The proximal end of the shaft 50 includes a hex socket 62 for receiving a driving tool for advancing the actuator assembly 18 with respect to the body 12. The distal end of the shaft 50 includes an actuator engagement portion 64 configured to connect to the actuator 48. The actuator engagement portion 64, as shown in FIG. 1f, is a projection that slides into a channel 66 on the actuator 48. Once inserted into the channel 66, movement of the shaft 50 solely along the longitudinal axis of the spacer 10 will not release the shaft 50 from the actuator 48. In one variation, the actuator 48 and shaft 50 are integrally formed.

Still referencing FIG. 1f, the retainer 52 is a circular ring preferably made of metal such as surgical steel or titanium. The retainer 52 fits into a recess 68 formed on the inner surface of the body 12. When pressed into the recess 68, the retainer 52 secures the actuator 48 inside the passageway 30 of the body 12. The actuator assembly 18 is at least partially disposed inside the body 12 and is configured for sliding engagement with respect to the body 12.

Assembly of the spacer 10 with reference to FIGS. 1a-1f will now be described. The arms 14, 16 are disposed in the arm receiving portion 24 of one body piece. The other of the left or right body piece 20, 22 is securely connected/welded to the one body piece thereby capturing the arms 14, 16 inside the arm receiving portion 24 such that the arms 14, 16 are capable of at least rotational movement with respect to the body 12 and in one variation, capable of rotational movement and translation with respect to the body 12. In a variation in which the body 12 is made of one piece, the arms 14, 16 are movably connected to the body 12 with a pin. The shaft 50 is connected to the actuator 48 and together inserted and threadingly connected into the passageway 30 of the body 12. The retainer 52 is passed over the proximal end of the shaft 50 and snapped into the recess 68 of the body 12 to secure the actuator assembly 18 inside the body 12 such that the actuator assembly 18 is capable of threaded translational movement with respect to the body 12.

Figure 4B:
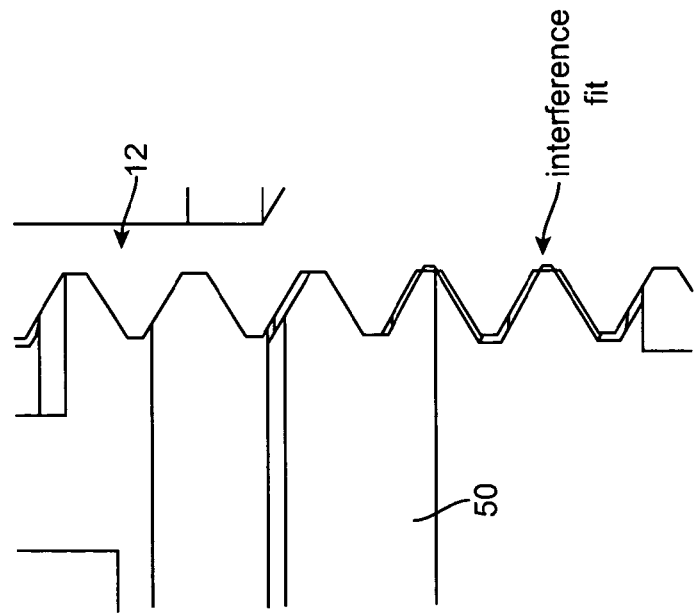
FIG. 4b illustrates a side view of a portion of a half of a body and actuator assembly of a spacer according to the present invention.
Figure 4A:
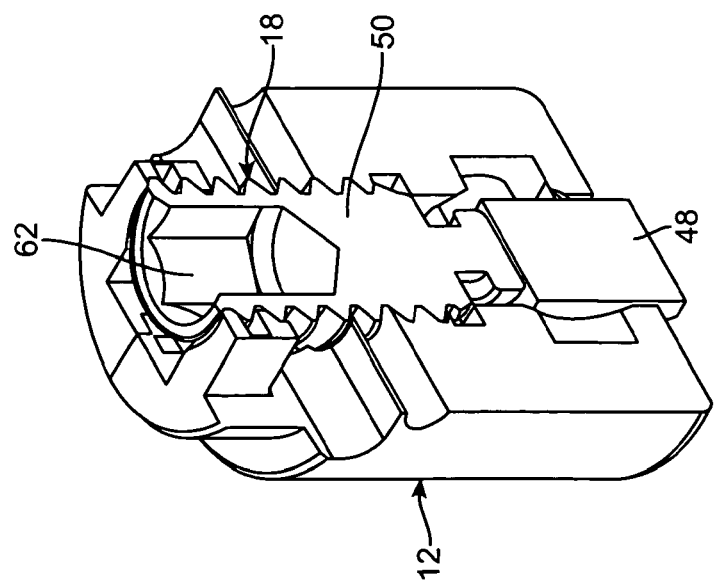
FIG. 4a illustrates a perspective view of a half of a body and actuator assembly of a spacer according to the present invention.

With particular reference to FIGS. 4a and 4b, in one variation, the threaded shaft 50 contacts the threaded inner surface of the body 12 in an interference fit engagement wherein the inner diameter of the body threads is smaller than the root diameter of the shaft threads as shown in FIG. 4b. This interference helps prevent the shaft 50 from loosening and backing-up out of the body 12 which would result in folding of the arms 14, 16. The interference is created with the threads of the shaft 50 and one or more of the distally located threads along the body 12 such that when advancement of the shaft 50 nears complete deployment (at approximately 90 degrees splaying of the arms 14, 16 with respect to the body 12) the distally located "interference" threads are engaged to tighten the shaft 50 to the body 12, thereby, providing an interference lock which is reversible by turning the shaft in the opposite direction. The interference lock with one or more of the distally located threads affords the surgeon flexibility in that the spacer 10 can be partially deployed and undeployed (via rotation of the shaft 50 in the opposite direction) repeatedly until the surgeon locates and properly seats the implant before locking it by advancing the shaft further into the section of the threads where the interference fit is created.

Referring now to FIGS. 5a-5d, the spacer 10 is shown in a closed, undeployed configuration (FIG. 5a), a partially deployed configuration or otherwise intermediary configuration (FIG. 5b), a deployed configuration (FIG. 5c), and a deployed and extended configuration (FIG. 5d). In moving from an undeployed to a deployed configuration, the actuator assembly 18, and in particular, the shaft 50 of the actuator assembly moves distally with respect to the body 12 and the shaft 50 advantageously moves to a position flush with the proximal end of the body 12 or to a position completely inside the body 12 disappearing from sight providing a low profile for the spacer 10 along the longitudinal axis of the body 12.

Figure 6C:
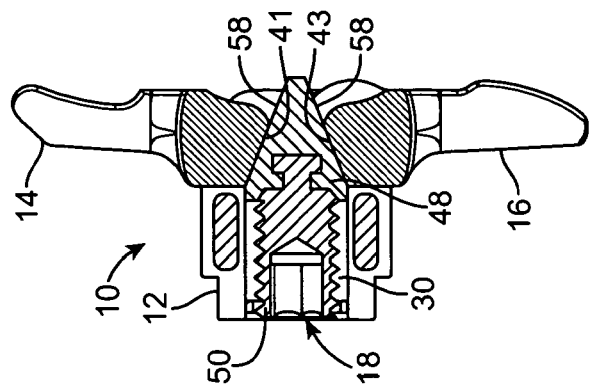
FIG. 6c illustrates a side, cross-sectional view of a spacer in a deployed and extended configuration according to the present invention.
Figure 6B:
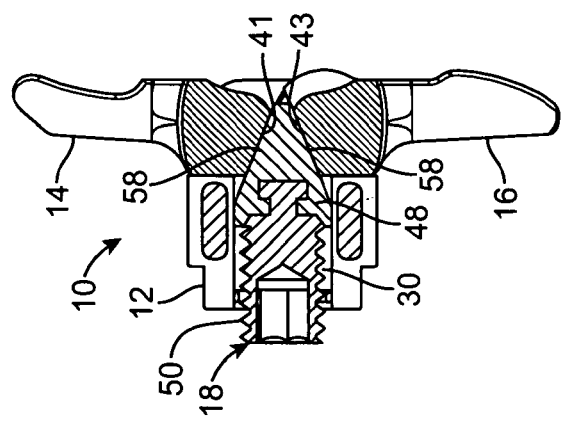
FIG. 6b illustrates a side, cross-sectional view of a spacer in a deployed configuration according to the present invention.
Figure 6A:
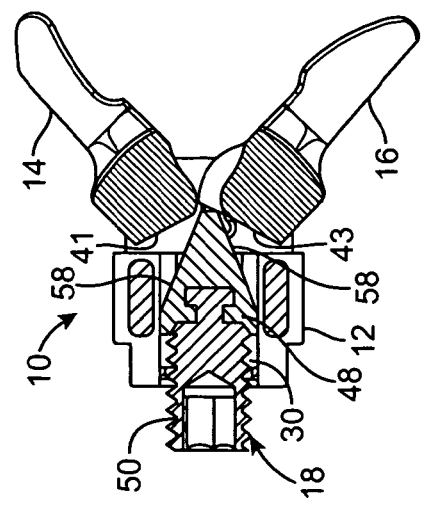
FIG. 6a illustrates a side, cross-sectional view of a spacer in a partially deployed configuration according to the present invention.
Figure 7C:
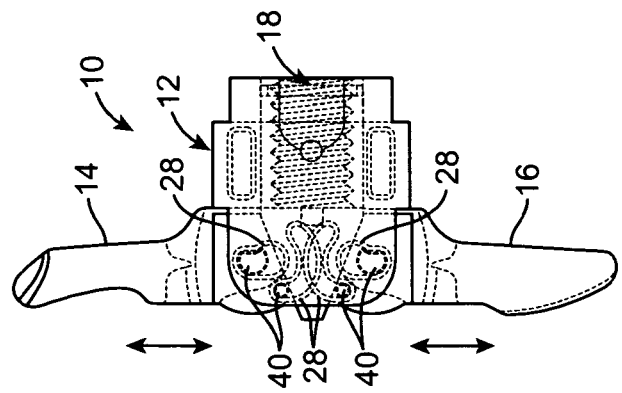
FIG. 7c illustrates a side, semi-transparent view of a spacer in a deployed and extended configuration according to the present invention.

Turning now to the cross-sectional views of the spacer 10 in FIGS. 6a-6c, as the shaft 50 advances within the passageway 30, the bearing surfaces 58 of the actuator 48 contact the superior and inferior caming surfaces 41, 43 of the superior and inferior arms 14, 16 turning the arms 14, 16 into rotation with respect to the body 12. Upon rotation, the bearing surfaces 58 of the actuator 48 slide with respect to the superior and inferior caming surfaces 41, 43 of the superior and inferior arms 14, 16. The arms 14, 16 rotate through an arc of approximately 90 degrees with respect to the body 12 into the deployed configuration (FIG. 6b) and with further actuation, into a deployed and extended configuration (FIG. 6c) in which the superior and inferior extensions of the arms 14, 16 are substantially perpendicular to the longitudinal axis of the spacer 10 as shown in FIGS. 6b and 6c.

Figure 7B:
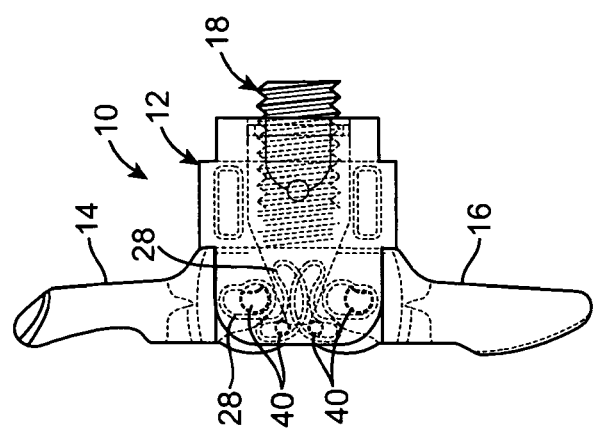
FIG. 7b illustrates a side, semi-transparent view of a spacer in a deployed configuration according to the present invention.
Figure 7A:
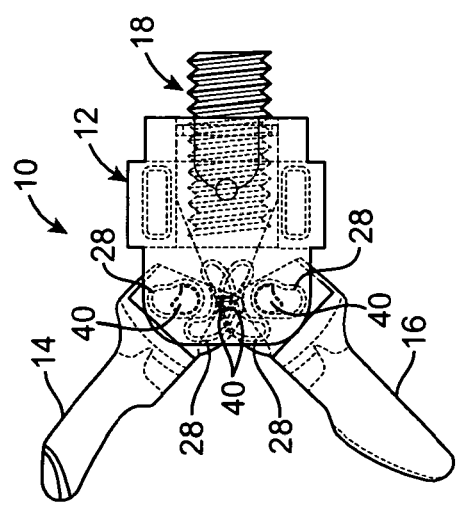
FIG. 7a illustrates a side, semi-transparent view of a spacer in a partially deployed configuration according to the present invention.

Turning now to the semi-transparent views of the spacer 10 in FIGS. 7a-7c, the rotation of the pins 40 of the arms 14, 16 in the slots 28 of the body 12 is shown in moving from the configuration of FIG. 7a to the configuration of FIG. 7b. The translation of the pins 40 of the arms 14, 16 in the elongated portion of the slots 28 of the body 12 is shown in moving from the deployed configuration of FIG. 7b to the deployed and extended configuration of FIG. 7c in the direction of the arrows in FIG. 7c. Such outward translation with respect to the body 12 is guided by the length and shape of the slots 28. Reverse rotation of the shaft 50 moves the shaft 50 proximally with respect to the body 12 allowing the arms to close to any intermediary configuration between a deployed, extended configuration and an undeployed, closed configuration. This feature advantageously permits the surgeon to ease installation and positioning of the spacer with respect to patient anatomy.

With reference to FIGS. 8a-8f, various views of another variation of a spacer 10 according to the present invention are shown wherein like reference numbers are used to describe like parts. The spacer 10 includes a body 12 connected to a superior extension member or arm 14, an inferior extension member or arm 16, and an actuator assembly 18.

Figure 9A:
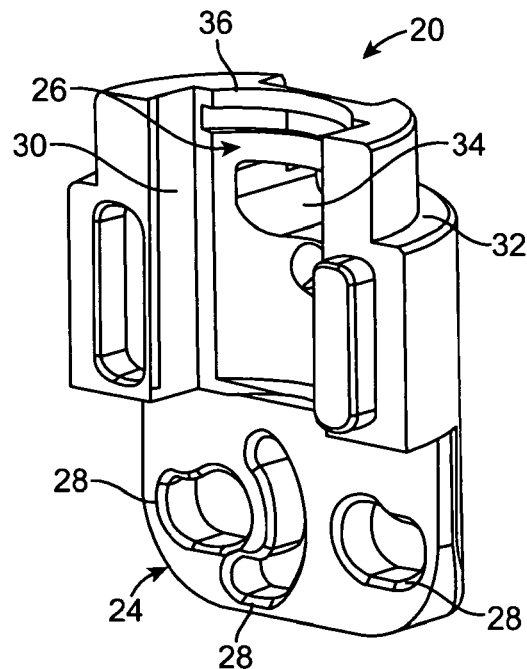
FIG. 9a illustrates a perspective view of half of a body of a spacer according to the present invention.
Figure 9B:
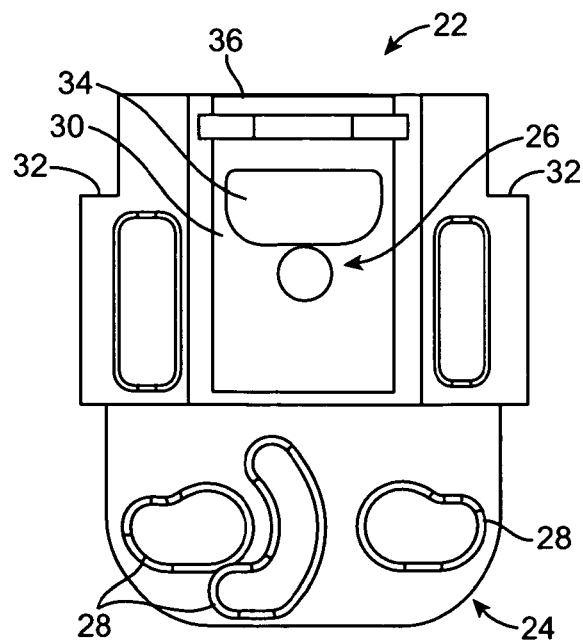
FIG. 9b illustrates a side view of half of a body of a spacer according to the present invention.

Turning now to FIGS. 9a and 9b, the body 12 will now be described. The body 12 is shown to have a clamshell construction with a left body piece 20 (shown in FIG. 9a) joined to a right body piece 22 (shown in FIG. 9b) to capture arms 14, 16 inside. With the right and left body pieces 20, 22 joined together, the body 12 is generally cylindrical. It has a cross-sectional size and shape that allows for implantation between adjacent spinous processes and facilitates delivery into a patient through a narrow port or cannula.

The inside of the body 12 defines an arm receiving portion 24 and an actuator assembly receiving portion 26 with features formed in each of the left and right body pieces 20, 22 that together define the arm and actuator assembly receiving portions 24, 26. In one variation, the arm receiving portion 24 includes slots or openings or apertures 28 that receive pins formed on the arms 14, 16 such that the pins rotate and/or translate inside the slots or apertures 28. The actuator assembly receiving portion 26 includes a passageway 30. Other features include a tongue and groove for mating with the opposite clamshell.

Figure 8A:
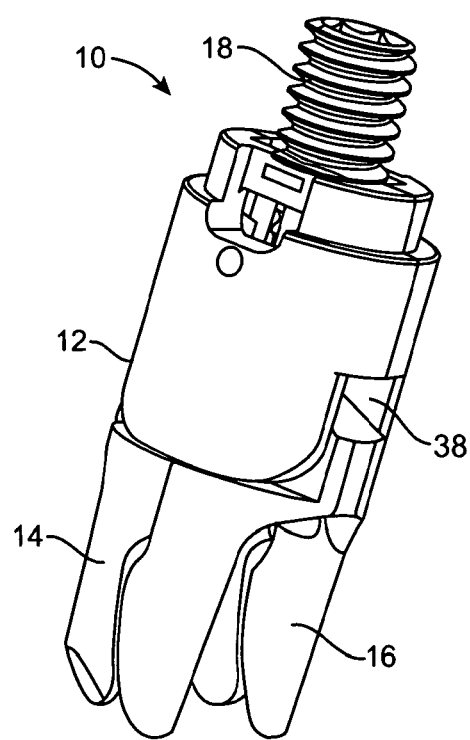
FIG. 8a illustrates a perspective view of a spacer according to the present invention.
Figure 8B:
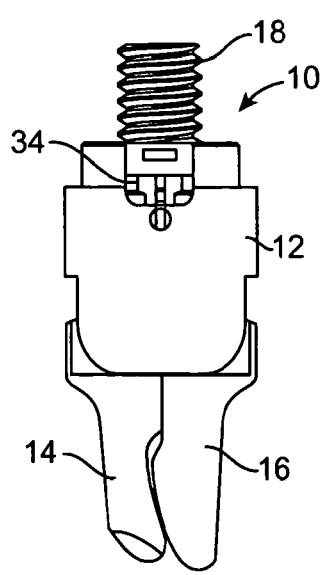
FIG. 8b illustrates a side view of a spacer according to the present invention.
Figure 8C:
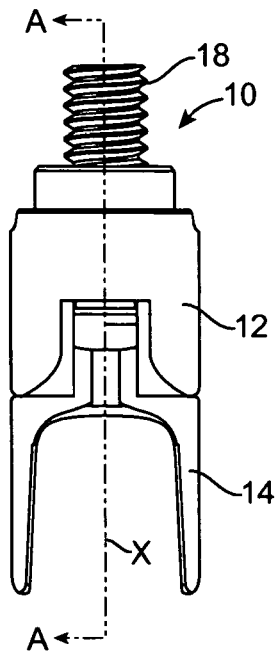
FIG. 8c illustrates a top view of a spacer according to the present invention.
Figure 8D:
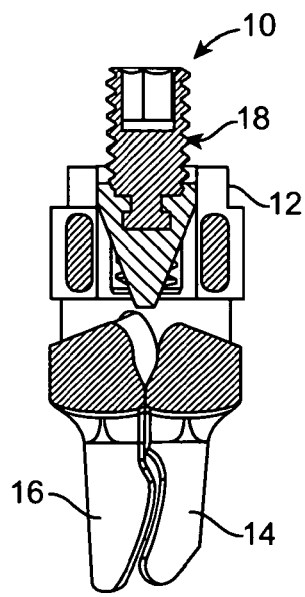
FIG. 8d illustrates a cross-sectional view of the spacer of FIG. 8c taken along line A-A according to the present invention.
Figure 8E:
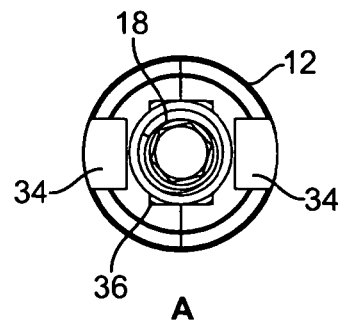
FIG. 8e illustrates an end view of a spacer according to the present invention.

The outside of the body 12 defines a ledge 32 along at least a portion of the periphery. Notches 34 are formed at opposite locations as also shown in FIG. 8b. The notches 34 are configured for pronged attachment to a spacer delivery instrument. When joined together, the left and right body pieces 20, 22 define a proximal opening 36 (as seen in FIG. 8e) and a distal opening 38 (as seen in FIG. 8a) in the body 12. A longitudinal scallop (not shown) extending from the proximal end of the spacer to the distal end is formed in the outer surface of the body 12 to facilitate placement of the spacer 10 between and to conform to the anatomy of adjacent interspinous processes.

Figure 10A:
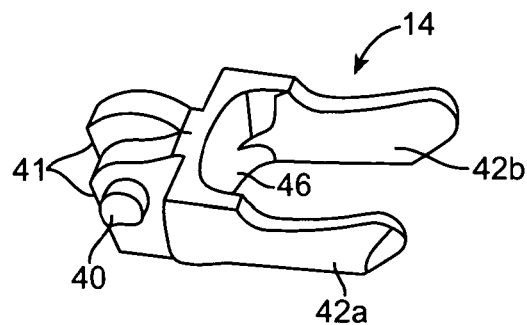
FIG. 10a illustrates a perspective view of a superior arm of a spacer according to the present invention.
Figure 10B:
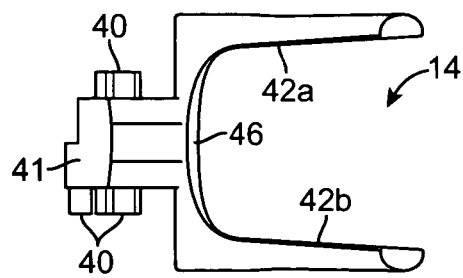
FIG. 10b illustrates a back view of a superior arm of a spacer according to the present invention.
Figure 10C:
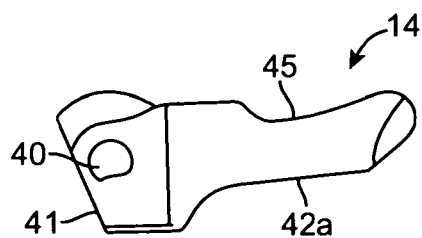
FIG. 10c illustrates a side view of a superior arm of a spacer according to the present invention.
Figure 10D:
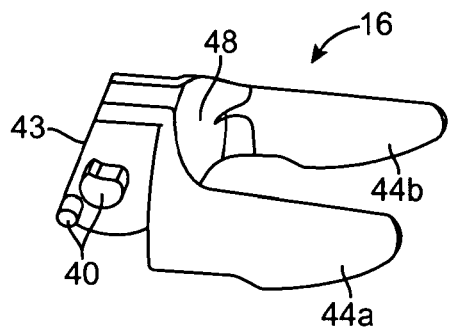
FIG. 10d illustrates a perspective view of an inferior arm of a spacer according to the present invention.
Figure 10E:
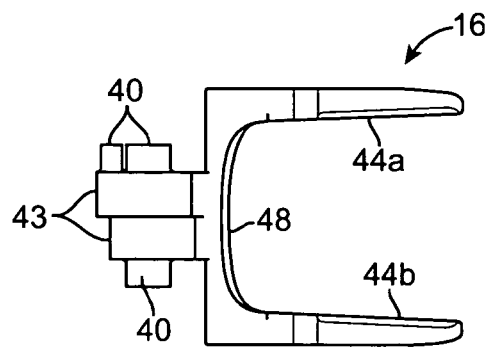
FIG. 10e illustrates a back view of an inferior arm of a spacer according to the present invention.
Figure 10F:
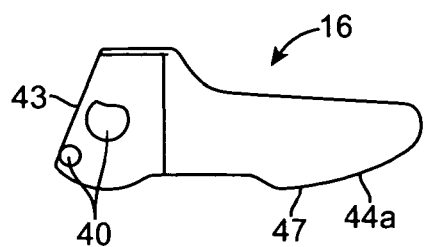
FIG. 10f illustrates a side view of an inferior arm of a spacer according to the present invention.

Turning now to FIGS. 10a-10c, the superior arm 14 is shown and in FIGS. 10d-10f, the inferior arm 16 is shown. The superior and inferior arms 14, 16, include pins 40 for mating with the body 12, in particular, for mating with the slots or apertures 28 of the arm receiving portion 24. Each of the superior and inferior arms 14, 16 includes at least one caming surface 41, 43, respectively, for contact with the actuator assembly 18. The superior and inferior arms 14, 16 include elongated superior extensions 42*a*, 42*b* and elongated inferior extensions 44*a*, 44*b*, respectively. Extensions 42*a* and 44*a* are located on the left adjacent to the left body piece 20 and extensions 42*b* and 44*b* are located on right adjacent to the right body piece 22. Superior extensions 42*a*, 42*b* extend substantially parallel to each other in both an undeployed configuration and in a deployed configuration as do inferior extensions 44*a*, 44*b*. Extending between extensions 42*a*, 42*b* is a strut, bridge, bracket or saddle 46 that forms a superior substantially U-shaped configuration that is sized and configured to receive a superior spinous process. As seen in FIG. 10*c*, the anterior face of the superior extensions 14 includes a slight concavity or curvature 45 for conforming to the bony anatomy of the superior spinous process and or lamina. Also, extending between inferior extensions 44*a*, 44*b* is a strut, bridge, bracket or saddle 48 that forms an inferior substantially U-shaped configuration together with the extensions 44*a*, 44*b* that is sized and configured to receive an inferior spinous process of a spinal motion segment. As seen in FIG. 10*f*, the anterior face of the inferior extensions 16 includes a slight convexity or curvature 47 for conforming to the bony anatomy of the inferior spinous process and or lamina.

The superior and inferior arms 14, 16 are movably or rotatably connected to the body 12, for example by hinge means or the like to provide rotational movement from an undeployed configuration to a deployed configuration in which the arms arc through about a 90 degree range or more with respect to the body 12. The arms 14, 16 are rotationally movable between at least an undeployed, collapsed or folded state (as shown in FIGS. 8*a*-8*e*) and at least one deployed state (as shown in FIGS. 12*c*, 12*d*, 13*b*, 13*c*, 14*b* and 14*c*). In the undeployed state, the arm pairs 14, 16 are aligned generally or substantially axially (i.e., axially with the longitudinal axis defined by the body 12 or to the translation path into the interspinous space of the patient) to provide a minimal lateral or radial profile. The longitudinal axis X of the spacer and body is shown in FIG. 8*c*. In the deployed state, the arm pairs 14, 16 are positioned such that each of the U-shaped saddles are in a plane(s) or have a U-shaped projection in a plane that is generally or substantially transverse to the longitudinal axis X defined by the body 12 or to the collapsed position or to the implantation path into the interspinous space of the patient. In one variation, the spacer 10 is configured such the arms 14, 16 are linearly moveable or translatable within the plane from a first deployed state (such as the state shown in FIGS. 12*c*, 13*b*, 14*b*) to and from a second deployed state (such as the state shown in FIG. 12*d*, 13*c*, 14*c*) characterized by an additional translation of at least one of the arms 14, 16 with respect to the body 12 along a direction of the arrows as shown in FIG. 14*c*. More specifically, the arms 14, 16 can be extended in the general vertical direction along an axis substantially parallel to the spine wherein the arms 14, 16 are extended away from each other and away from the body 12 as denoted by the arrows in FIG. 14*c*. This feature advantageously allows for the most minimally invasive configuration for the spacer without compromising the ability of the spacer 10 to seat and contain the spinous processes in between levels where the anatomy of the spinous processes is such that the interspinous process space increases in the anterior direction or without compromising the ability of the spacer to provide adequate distraction. The arms 14, 16 are connected to the body 12 and/or to each other in a manner that enables them to be moved simultaneously or independently of each other, as well as in a manner that provides passive deployment and/or vertical extension or, alternatively, active or actuated deployment and/or vertical extension.

Turning back to FIG. 8*f*, the actuator assembly 18 will now be described. The actuator assembly 18 includes an actuator 48 connected to a shaft 50 and retainer 52. The actuator 48 includes a distal end 54 and a proximal end 56 and at least two bearing surfaces 58. The bearing surfaces 58 angle towards each other from the proximal end 54 towards the distal end 56. The proximal end 54 of the actuator 48 includes a shaft receiving portion 60 configured to receive the shaft 50. The distal end of the actuator 48 is further configured to engage the superior and inferior arms 14, 16 such that forward translation of the actuator 48 relative to the body 12 effects deployment of the arms into at least one deployed configuration.

Figure 8F:
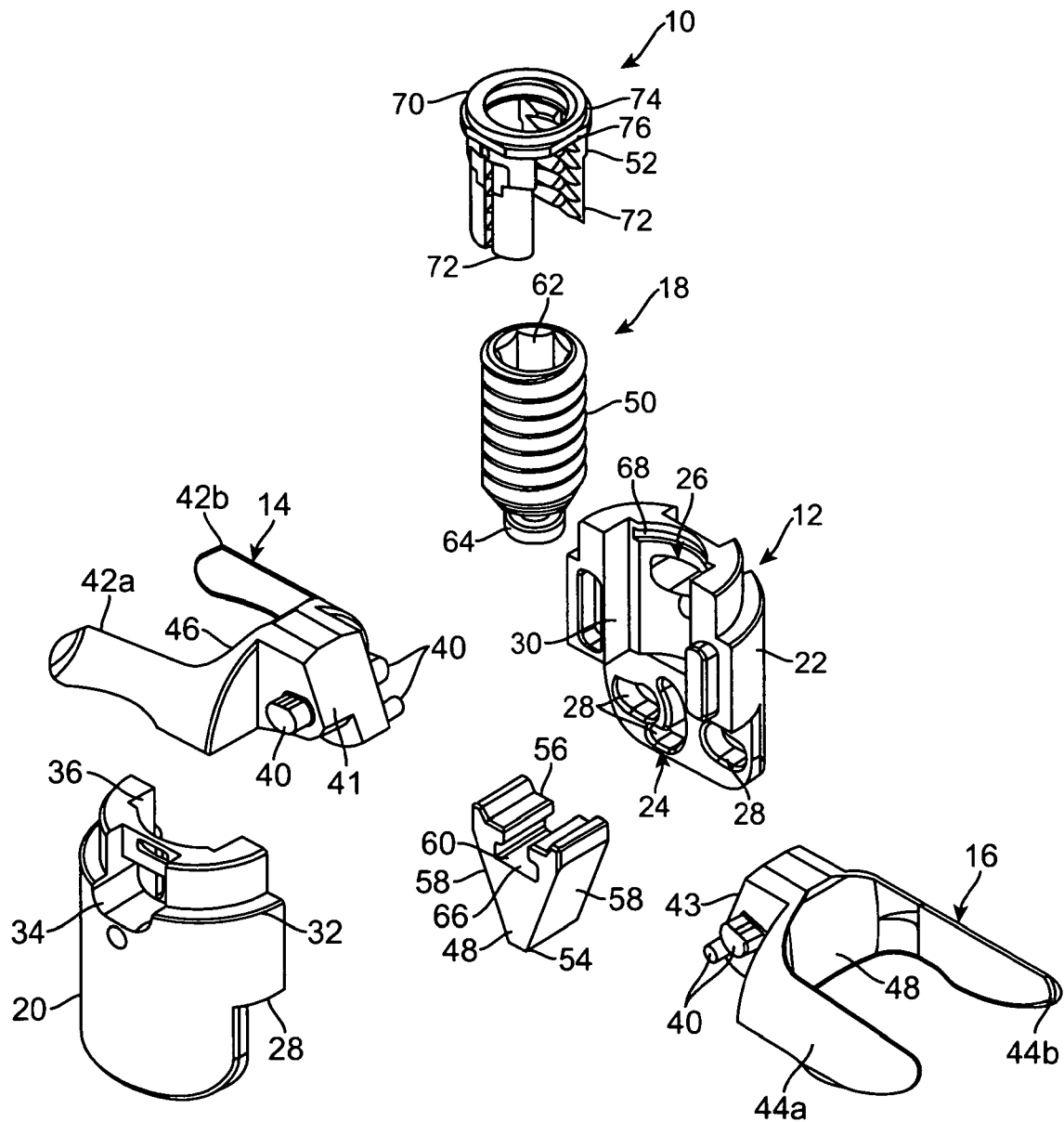
FIG. 8f illustrates an exploded perspective view of a spacer according to the present invention.

Still referencing FIG. 8*f*, the shaft 50 is substantially cylindrical in shape and includes a threaded outer surface for engagement with a threaded inner surface of the retainer 52. The proximal end of the shaft 50 includes a hex socket 62 for receiving a driving tool for advancing the actuator assembly 18 with respect to the body 12 to deploy the arms 14, 16. The distal end of the shaft 50 includes an actuator engagement portion 64 configured to connect to the actuator 48. The actuator engagement portion 64 as shown in FIG. 8*f*, is a projection that slides into a channel 66 on the actuator 48. Once inserted into the channel 66, movement of the shaft 50 solely along the longitudinal axis of the spacer 10 will not release the shaft 50 from the actuator 48. In one variation, the actuator 58 and shaft 50 are integrally formed.

Still referencing FIG. 8*f*, the retainer 52, which is preferably made of metal such as surgical steel or titanium, includes a circular proximal end 70 and two prongs 72 extending distally from the circular proximal end 70 configured to received the shaft 50. Clearance for the passage of the actuator 48 is provided between the prongs 72. Threads are formed on the inner surface of the prongs 72 for conformal engagement with the threads on the shaft 50 such that the shaft 50 may threadingly pass through the retainer 52. In one variation each prong 72 is split down the middle as shown in FIG. 8*f*. A ledge 74 is formed along at least a portion of the periphery of the retainer 52 at the proximal end. The ledge 74 of the retainer 52 fits into a recess 68 formed on the inner surface of the body 12. When pressed into the recess 68, the retainer 52 is secured to the body 12 and the retainer 52 in turn secures the actuator 48 inside the passageway 30 of the body 12. Alignment flats 76 are formed at locations opposite to each other on the outer surface of the retainer 52. The alignment flats 76 keep the threaded insert aligned with the body 12.

Assembly of the spacer 10 with reference to FIG. 8*f* will now be described. The arms 14, 16 are disposed in the arm receiving portion 24 of one body piece. The other of the left or right body piece 20, 22 is securely connected/welded to the one body piece thereby capturing the arms 14, 16 inside the arm receiving portion 24 such that the arms 14, 16 are capable of rotational movement with respect to the body 12 and, in one variation, capable of rotational movement and translation with respect to the body 12. The shaft 50 threaded into the retainer 52 and connected to the actuator 58. The retainer 52 and the actuator 48 and shaft 50 are inserted into the passageway 30 of the body 12 and the retainer 52 is snapped inside the recess 68 of the body 12 to secure the actuator 48 inside the body 12 such that the actuator assembly 18 is capable of threaded translational movement with respect to the body 12.

Figure 11B:
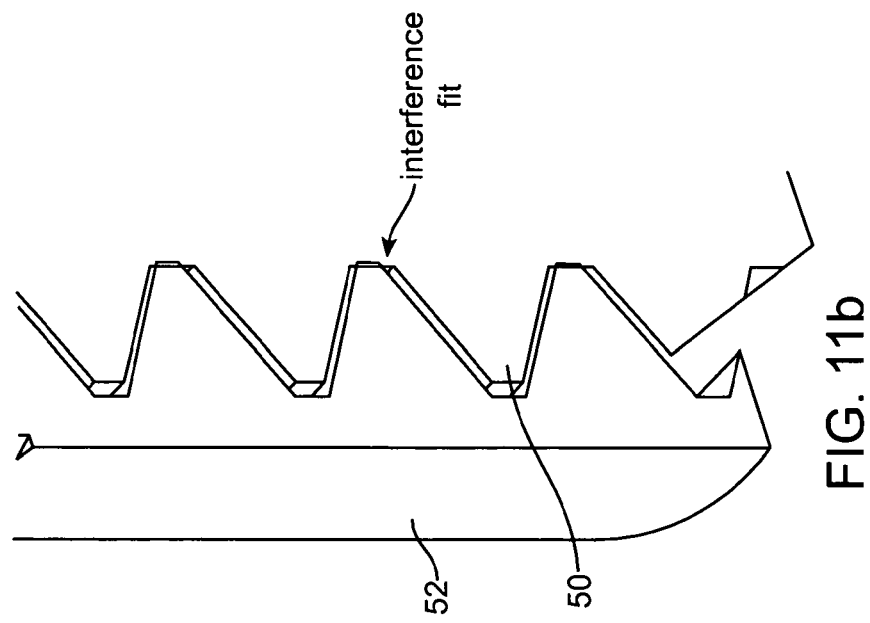
FIG. 11b illustrates a side view of a portion of an actuator shaft and retainer of a spacer according to the present invention.
Figure 11A:
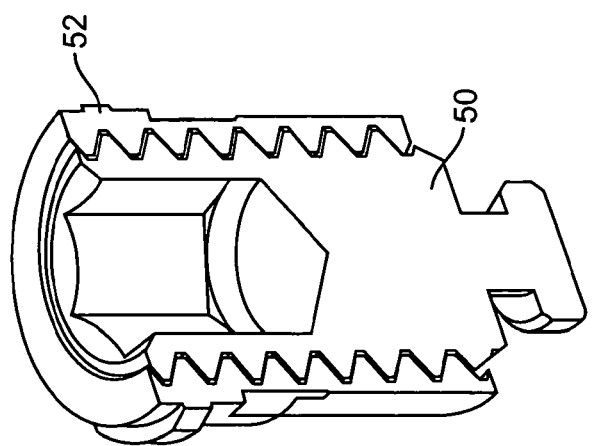
FIG. 11a illustrates a perspective view of a half of an actuator shaft and retainer of a spacer according to the present invention.

With particular reference to FIGS. 11*a* and 11*b*, the threaded shaft 50 contacts the threaded inner surface of the retainer 52 in an interference fit engagement wherein the inner diameter of the retainer threads is smaller than the root diameter of the shaft threads as shown in FIG. 11b. This interference helps prevent the shaft 50 from loosening and backing-up out of the body 12 which would result in folding of the arms 14, 16. The interference is created with the threads of the shaft 50 and one or more of the threads along the retainer 52 such that when advancement of the shaft 50 nears complete deployment (at approximately 90 degrees splaying of the arms 14, 16 with respect to the body 12) the distally located "interference" threads relative to the more proximally located non-interference threads of the same retainer 52 are engaged to tighten the shaft 50 to the retainer 52 and in turn to the body 12, thereby, providing an interference lock which is reversible by turning the shaft in the opposite direction. The prongs 72 of the retainer 52 advantageously and reversibly flex outwardly and inwardly instead of plastically deforming. This feature allows the implant to be repeatedly locked and unlocked without wearing out the threads and thereby preserving the interference lock feature. The interference lock with one or more of the distally located threads affords the surgeon flexibility in that the spacer 10 can be partially deployed and undeployed (via rotation of the shaft 50 in the opposite direction) repeatedly until the surgeon locates and properly seats the implant before locking it by advancing the shaft further into the section of the threads where the interference fit is created.

Referring now to FIGS. 12a-12d, the spacer 10 is shown in a closed, undeployed configuration (FIG. 12a), a partially deployed configuration, or intermediary configuration (FIG. 12b), a deployed configuration (FIG. 12c), and a deployed and extended configuration (FIG. 12d). In moving from an undeployed to a deployed configuration, the actuator assembly 18, and in particular, the shaft 50 of the actuator assembly moves distally with respect to the body 12 and the shaft 50 advantageously moves to a position flush with the proximal end of the body 12 or to a position completely inside the body 12 disappearing from sight providing a low profile for the spacer 10 along the longitudinal axis of the body 12.

Figure 13C:
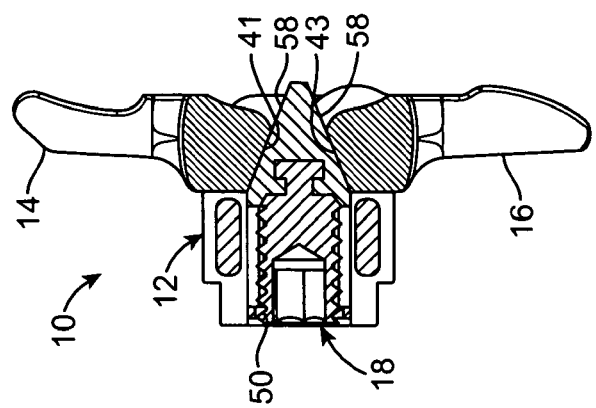
FIG. 13c illustrates a side, cross-sectional view of a spacer in a deployed and extended configuration according to the present invention.
Figure 13B:
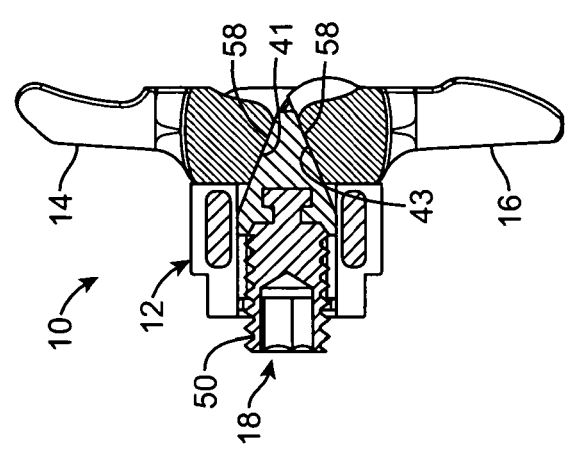
FIG. 13b illustrates a side, cross-sectional view of a spacer in a deployed configuration according to the present invention.
Figure 13A:
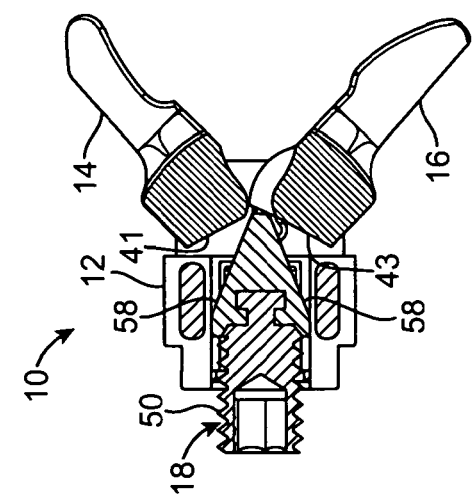
FIG. 13a illustrates a side, cross-sectional view of a spacer in a partially deployed configuration according to the present invention.
Figure 14C:
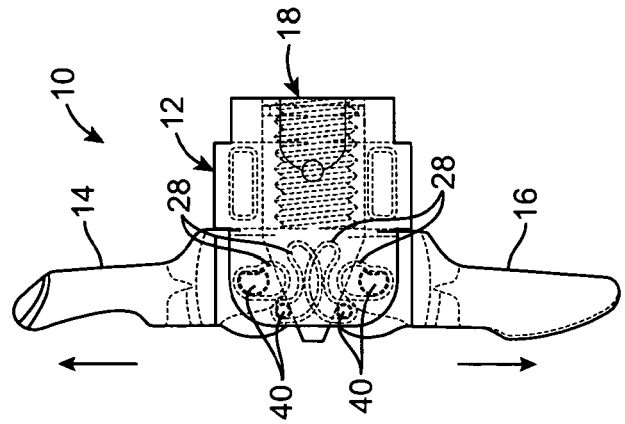
FIG. 14c illustrates a side, semi-transparent view of a spacer in a deployed and extended configuration according to the present invention.

Turning now to the cross-sectional views of the spacer 10 in FIGS. 13a-13c, as the shaft 50 advances within the passageway 30, the bearing surfaces 58 of the actuator 48 contact the superior and inferior caming surfaces 41, 43 of the superior and inferior arms 14, 16 turning the arms 14, 16 into rotation with respect to the body 12. Upon rotation, the bearing surfaces 58 of the actuator 48 slide with respect to the superior and inferior caming surfaces 41, 43 of the superior and inferior arms 14, 16. The arms 14, 16 rotate through an arc of approximately 90 degrees with respect to the body 12 into the deployed configuration (FIG. 13b) and with further actuation, into a deployed and extended configuration (FIG. 13c) in which the superior and inferior extensions of the arms 14, 16 are substantially perpendicular to the longitudinal axis of the spacer 10 as shown in FIGS. 13b and 13c.

Figure 14B:
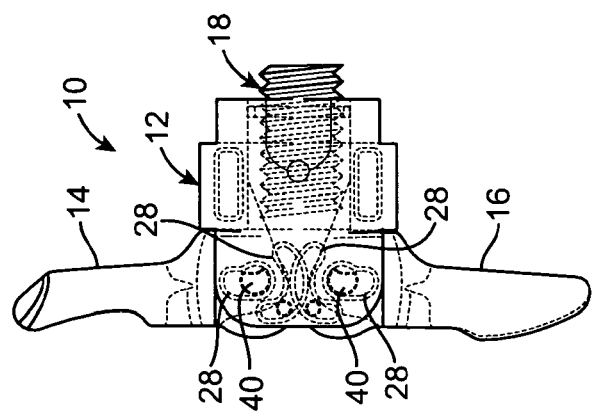
FIG. 14b illustrates a side, semi-transparent view of a spacer in a deployed configuration according to the present invention.
Figure 14A:
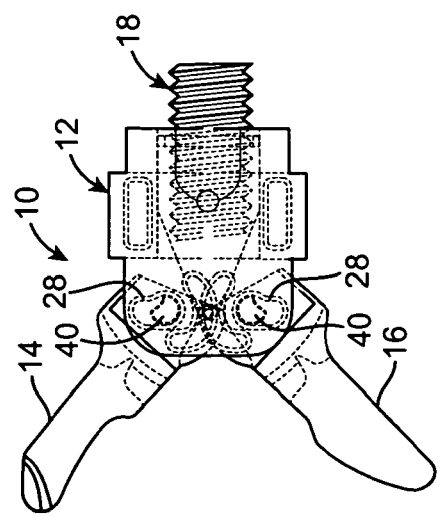
FIG. 14a illustrates a side, semi-transparent view of a spacer in a partially deployed configuration according to the present invention.

Turning now to the semi-transparent views of the spacer 10 in FIGS. 14a-14c, the rotation of the pins 40 of the arms 14, 16 in the slots 28 of the body 12 is shown in moving from the configuration of FIG. 14a to the configuration of FIG. 14b. The translation of the pins 40 of the arms 14, 16 in the elongated portion of the slots 28 of the body 12 is shown in moving from the deployed configuration of FIG. 14b to the deployed and extended configuration of FIG. 14c in the direction of the arrows in FIG. 14c. Such outward translation with respect to the body 12 is guided by the length and shape of the slots 28. Reverse rotation of the shaft 50 moves the shaft 50 proximally with respect to the body 12 allowing the arms to close to any intermediary configuration between a deployed, extended configuration and an undeployed, closed configuration. This feature advantageously permits the surgeon to ease installation and positioning of the spacer with respect to patient anatomy.

The spacer of FIGS. 8-14 is delivered and deployed in the same manner as the spacer of FIGS. 1-7. To deliver and deploy the spacer 10 within the patient, the spacer 10 is releasably attached to an insertion instrument 80 at the proximal end of the spacer 10 via notches 34. The insertion instrument 80 includes a first assembly 102 connected to a second assembly 104 and a handle assembly 106.

Figure 15A:
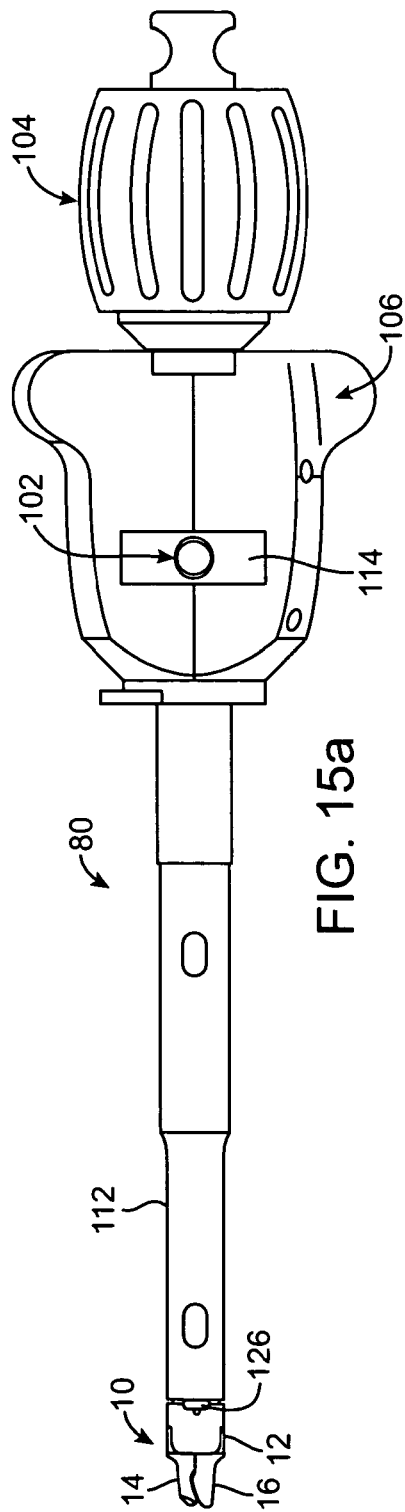
FIG. 15a illustrates a side view of an insertion instrument connected to a spacer in a closed, undeployed configuration according to the present invention.

The spacer 10 is provided or otherwise placed in its undeployed, closed state in juxtaposition to the insertion instrument 80 and connected thereto as shown in FIG. 15a. The longitudinal axis of the insertion instrument 80 is advantageously substantially aligned with the longitudinal axis of the spacer 10 as shown. The delivery instrument 80 includes a first subassembly 102 to releasably clamp to the body 12 of the spacer 10 at a distal end of the insertion instrument 80. The first subassembly 102 includes an inner clamp shaft (not shown) having flexible prongs 126 at the distal end configured for attachment to the body 12 of the spacer 10 and, in particular, for insertion into the notches 34 of the spacer body 12. The first subassembly 102 includes an outer shaft 112 located over the inner clamp shaft and configured for relative motion with respect to one another via a control 114 located at the handle assembly 106. The control 114 is threaded to the outer shaft 112 such that rotation of the control 114 moves the outer shaft 112 along the longitudinal axis of the insertion instrument 80 over the inner clamp shaft to deflect and undeflect the prongs 126 to connect or disconnect the instrument 80 to or from the body 12. The first control 114 is activated at the handle of the insertion instrument 100 such that the first subassembly 102 is connected to the body 12 of the spacer 10. The first control 114 is rotated in one direction to advance the outer shaft 112 over the inner clamp shaft 110 deflecting the prongs 118 inwardly into the notches 34 on the body of the spacer 12 to secure the spacer body 12 to the instrument as shown clearly in FIG. 15a. Reverse rotation of the control 114 reverses the direction of translation of the outer shaft 112 to release the prongs 126 from the notches 34 and, thereby, release the spacer 10 from the instrument 80.

Still referencing FIG. 15a, the insertion instrument 80 includes a second subassembly 104 that is configured to connect to the actuator assembly 18 of the spacer 12. In particular, the second subassembly 104 includes means located at the distal end of the second subassembly 104 to activate the actuator assembly 18. In one variation, the second subassembly 104 is a hexagonal-shaped driver having an elongated shaft that is configured to be insertable into the hex socket 62 of the shaft 50 while the spacer 10 is connected to the instrument 80. The second subassembly 104 is insertable at the proximal end of the instrument 80 and extends through the handle assembly 106 and through the inner shaft. The removable driver 104 is rotatable with respect to the instrument 80 to arrange the spacer 10 to and from deployed and undeployed configurations.

Figure 15B:
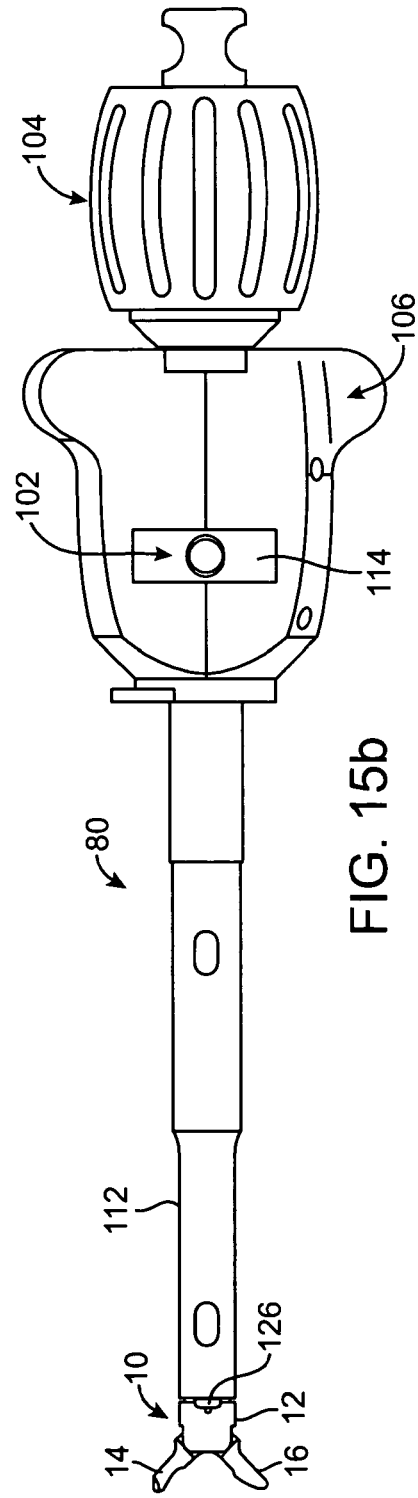
FIG. 15b illustrates a side view of an insertion instrument connected to a spacer in a partially deployed configuration according to the present invention.

To deliver and deploy the spacer 10 within the patient, the spacer 10 is releasably attached to a delivery instrument 80 at the proximal end of the spacer 10 as described. A small midline or lateral-to-midline incision is made in the patient for minimally-invasive percutaneous delivery. In one variation, the supraspinous ligament is split longitudinally along the direction of the tissue fibers to create an opening for the instrument. Dilators may be further employed to create the opening. In the undeployed state with the arms 14, 16 in a closed orientation and attached to a delivery instrument, the spacer 10 is inserted into a port or cannula, if one is employed, which has been operatively positioned to an interspinous space within a patient's back and the spacer is passed through the cannula to the interspinous space between two adjacent vertebral bodies. The spacer 10 is advanced beyond the end of the cannula or, alternatively, the cannula is pulled proximately to uncover the spacer 10 connected to the instrument 80. Once in position, the second assembly 104 is inserted into the instrument 80 and is rotated to begin the deployment of at least one of the superior arm 14 and inferior arm 16 or both simultaneously. FIG. 15b illustrates the superior arm 14 and the inferior arm 16 in a partially deployed position with the arms 14, 16 rotated away from the longitudinal axis. Rotation of the driver 104 turns the actuator shaft 50 advancing it with respect to the body 12 which distally advances the actuator 48 whose bearing surfaces 58 contact the superior and inferior camming surfaces 41, 43 pushing the superior and inferior arms 14, 16 into rotation about the pins 40. The position of the arms 14, 16 in FIG. 15b may be considered to be one of many partially deployed configurations or intermediary configurations that are possible and from which the deployment of the arms 14, 16 is reversible with opposite rotation of the second assembly 104.

Figure 15C:
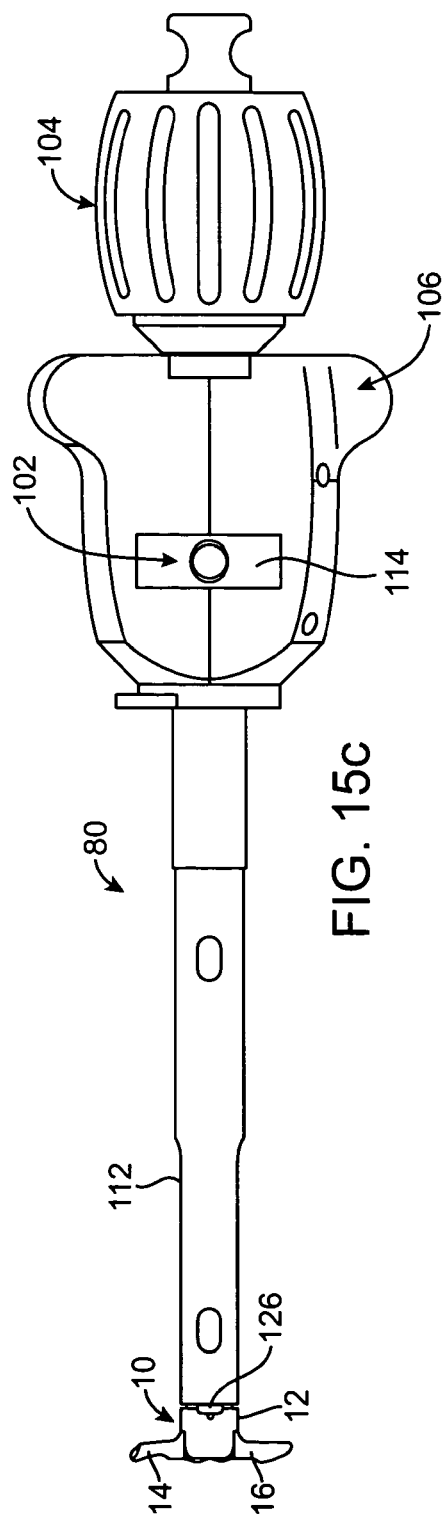
FIG. 15c illustrates a side view of an insertion instrument connected to a spacer in a deployed configuration according to the present invention.

Turning to FIG. 15c, there is shown an insertion instrument 80 connected to a spacer 10 in a first deployed configuration in which the arms 14, 16 are approximately 90 degrees perpendicular to the longitudinal axis or perpendicular the initial undeployed configuration. Continued rotation of second assembly 104 threads the shaft 50 further distally with respect to the body 12 of the spacer 10 pushing the bearing surfaces 58 further against the superior and inferior camming surfaces 41, 43. While in the first deployed configuration, the clinician can observe with fluoroscopy the positioning of the spacer 10 inside the patient and then choose to reposition the spacer 10 if desired. Repositioning of the spacer may involve undeploying the arms 14, 16 rotating them into any one of the many undeployed configurations. The spacer may then be re-deployed into the desired location. This process can be repeated as necessary until the clinician has achieved the desired positioning of the spacer in the patient.

Figure 15D:
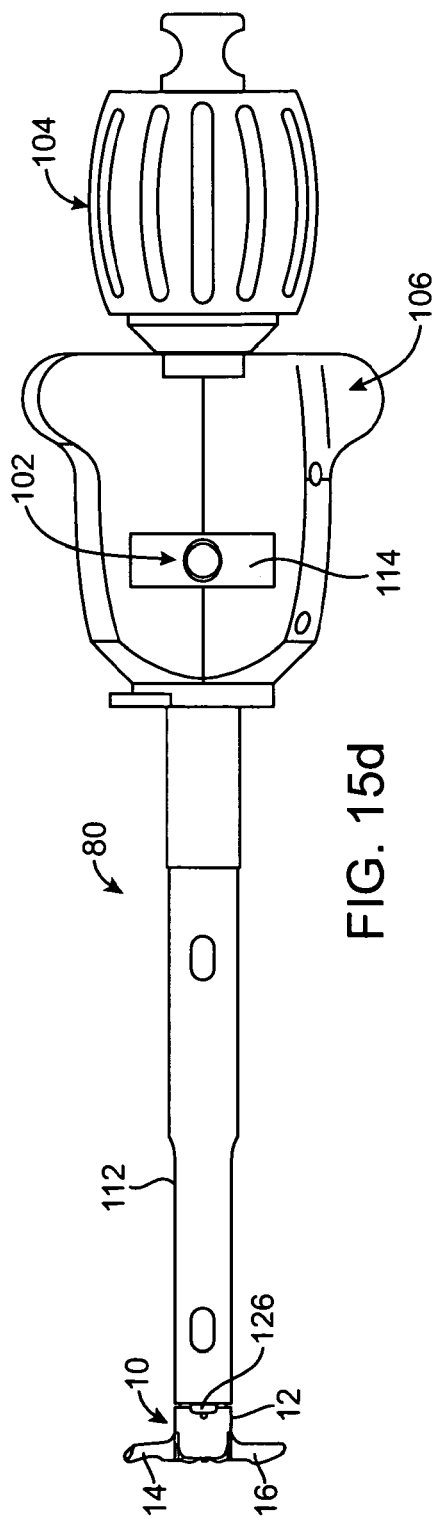
FIG. 15d illustrates a side view of an insertion instrument connected to a spacer in a deployed and extended configuration according to the present invention.

Even further advancement of the actuator shaft 50 via rotation of the second subassembly 104 from the first deployed configuration results in the spacer 10 assuming a second deployed configuration shown in FIG. 15d. The second deployed configuration is an extended configuration in which the superior and inferior arms 14, 16 extend transversely with respect to the longitudinal axis outwardly in the direction of the arrows in FIG. 14c. Such extension is guided by the length and shape of the slots 28 in which the arms 14, 16 move. Once deployed, the superior arm 14 seats the superior spinous process and the inferior arm 16 seats the adjacent inferior spinous process. Such extension may also provide some distraction of the vertebral bodies.

Figure 16:
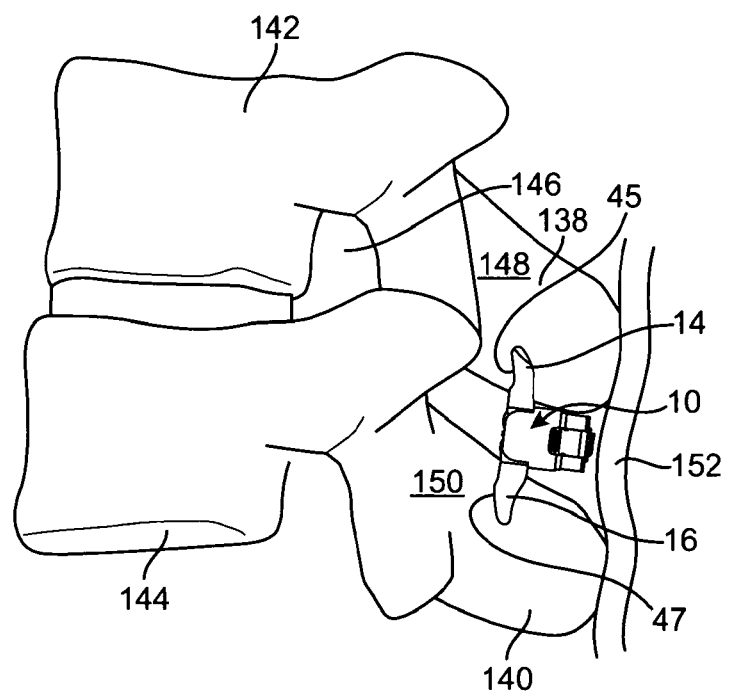
FIG. 16 illustrates a spacer according to the present invention deployed in an interspinous process space between two vertebral bodies and a supraspinous ligament.

Following deployment, the second assembly 104 may be removed. Control 114 is rotated in the opposite direction to release the body 12 from the instrument 80. The insertion instrument 80, thus released from the spacer 10, is removed from the patient leaving the spacer 10 implanted in the interspinous process space as shown in FIG. 16. In FIG. 16, the spacer 10 is shown with the superior arm 14 seating the superior spinous process 138 of a first vertebral body 142 and the inferior arm 16 seating the inferior spinous process 140 of an adjacent second vertebral body 144 providing sufficient distraction to open the neural foramen 146 to relieve pain. As mentioned above, the shape of the superior arm 14 is such that a superior concavity or curvature 45 is provided to conform to the widening of the superior spinous process 138 in an anterior direction toward the superior lamina 148 going in the anterior direction. In general, the superior arm 14 is shaped to conform to anatomy in the location in which it is seated. Likewise, as mentioned above, the shape of the inferior arm 16 is such that an inferior convexity or curvature 47 is provided to conform to the widening of the inferior spinous process 140 in an anterior direction toward the inferior lamina 150. The supraspinous ligament 152 is also shown in FIG. 20

The spacer 10 is as easily and quickly removed from body of the patient as it is installed. The instrument 80 is inserted into an incision and reconnected to the spacer 10. The shaft 50 is rotated in the opposite direction via a driver 104 to fold the arms 14, 16 into a closed or undeployed configuration. In the undeployed configuration, the spacer 10 can be removed form the patient along with the instrument 80 or, of course, re-adjusted and re-positioned and then re-deployed as needed with the benefit of minimal invasiveness to the patient.

Any of the spacers disclosed herein are configured for implantation employing minimally invasive techniques including through a small percutaneous incision and through the superspinous ligament. Implantation through the superspinous ligament involves selective dissection of the superspinous ligament in which the fibers of the ligament are separated or spread apart from each other in a manner to maintain as much of the ligament intact as possible. This approach avoids crosswise dissection or cutting of the ligament and thereby reduces the healing time and minimizes the amount of instability to the affected spinal segment. While this approach is ideally suited to be performed through a posterior or midline incision, the approach may also be performed through one or more incisions made laterally of the spine with or without affect to the superspinous ligament. Of course, the spacer may also be implanted in a lateral approach that circumvents the superspinous ligament altogether as well as in open or mini-open procedures.

Other variations and features of the various mechanical spacers are covered by the present invention. For example, a spacer may include only a single arm which is configured to receive either the superior spinous process or the inferior spinous process. The surface of the spacer body opposite the side of the single arm may be contoured or otherwise configured to engage the opposing spinous process wherein the spacer is sized to be securely positioned in the interspinous space and provide the desired distraction of the spinous processes defining such space. The additional extension of the arm(s) subsequent to their initial deployment in order to seat or to effect the desired distraction between the vertebrae may be accomplished by expanding the body portion of the device instead of or in addition to extending the individual extension members 14, 16.

The extension arms of the subject device may be configured to be selectively movable subsequent to implantation, either to a fixed position prior to closure of the access site or otherwise enabled or allowed to move in response to normal spinal motion exerted on the device after deployment. The deployment angles of the extension arms may range from less than 90 degrees (relative to the longitudinal axis defined by the device body) or may extend beyond 90 degrees and remain stationary or be dynamic. Each extension member may be rotationally movable within a range that is different from that of the other extension members. Additionally, the individual superior and/or inferior extensions 42a, 42b, 44a, 44b may be movable in any direction relative to the strut or bridge extending between an arm pair or relative to the device body in order to provide shock absorption and/or function as a motion limiter, or serve as a lateral adjustment particularly during lateral bending and axial rotation of the spine. The manner of attachment or affixation of the extensions to the arms may be selected so as to provide movement of the extensions that is passive or active or both. In one variation, the saddle or distance between extensions 42a and 42b or between 44a and 44b can be made wider to assist in seating the spinous process and then narrowed to secure the spinous process positioned between extensions 42a and 42b or between 44a and 44b.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A spacer, comprising a body;
   a first arm having a first portion and a second portion coupled to the first portion of the first arm;
   a second arm having a first portion and a second portion coupled to the first portion of the second arm, wherein the second portions of the first and second arms are attached to the body and the first portions of the first and second arms are disposed outside of the body in both an implantation position and a deployed position, wherein the first portions of the first and second arms each comprise a bridge and two extensions extending from the bridge; and
   an actuator assembly coupled to the body, the actuator assembly comprising a threaded shaft configured to rotate relative to the body and an actuator coupled to the threaded shaft and configured to move laterally as the threaded shaft is rotated, the actuator comprising two opposing bearing surfaces configured to respectively engage the first and second arms and to move the first portions of the first and second arms away from each other as the threaded shaft is rotated in a first direction from the implantation position towards the deployed position,
   wherein, when the spacer is disposed between a first vertebra and a second vertebra and the threaded shaft is rotated to the deployed position, the two extensions of the first portion of the first arm are configured to receive a portion of the first vertebra therebetween and the two extensions of the first portion of the second arm are configured to receive a portion of the second vertebra therebetween.

2. The spacer of claim 1, wherein the first and second arms are configured for rotation with respect to the body.

3. The spacer of claim 1, wherein the body comprises a plurality of notches defined therein and configured for attachment to prongs of an insertion instrument.

4. The spacer of claim 1, wherein the actuator assembly is configured to move the first portions of the first and second arms toward each other as the threaded shaft is rotated in a second direction, opposite the first direction, after the first portions of the first and second arms have been moved away from each other.

5. The spacer of claim 1, wherein the threaded shaft comprises a socket configured for engagement by a drive element of an insertion instrument for rotating the threaded shaft using the drive element.

6. The spacer of claim 5, wherein the socket is a hex socket.

7. A method for implanting the spacer of claim 1, the method comprising:
   moving the spacer into a subject by inserting the spacer through a supraspinous ligament of the subject to position the spacer directly between the first vertebra of the subject and the second vertebra of the subject; and
   rotating, in the first direction, the threaded shaft that is coupled to the body of the spacer, wherein the rotating laterally moves the actuator, which is coupled to the threaded shaft, relative to the body so that the actuator engages and moves the first portions of the first and second arms away from each other and into engagement with the first vertebra and second vertebra, respectively.

8. The method of claim 7, further comprising rotating, in a second direction opposite the first direction, the threaded shaft to move the first portions of the first and second arms toward each other after the first and second arms have been moved away from each other.

9. The method of claim 7, wherein the rotating comprises rotating the first and second arms with respect to the body.

10. The method of claim 7, further comprising attaching an insertion instrument to the body of the spacer prior to moving the spacer into the subject.

11. The method of claim 10, wherein the attaching comprises engaging a plurality of notches defined by the body of the spacer using prongs extending from a distal end portion of a shaft of the insertion instrument.

12. The method of claim 10, further comprising detaching the insertion instrument from the body of the spacer after rotating the threaded shaft to the deployment position.

13. The method of claim 7, wherein the rotating comprises engaging the threaded shaft with a drive element of an insertion instrument to rotate the threaded shaft using the drive element.

14. The method of claim 13, wherein the engaging comprises inserting a distal end portion of the drive element into a socket of the threaded shaft.

15. The method of claim 14, wherein the socket is a hex socket.

16. A kit, comprising
   the spacer of claim 1; and
   an insertion instrument comprising a shaft having a distal end portion and a proximal end portion and a drive element extending along the shaft and configured to engage the threaded shaft of the actuator assembly of the spacer and rotate the threaded shaft in the first direction.

17. The kit of claim 16, wherein the body of the spacer defines notches therein and the insertion instrument further comprises a plurality of prongs extending form the distal end portion of the shaft and configured for engaging the notches.

18. The kit of claim 16, wherein the threaded shaft comprises a socket configured for engagement by a drive element.

19. The kit of claim 18, wherein the socket is a hex socket.

* * * * *